United States Patent
Zhang et al.

(10) Patent No.: US 11,369,583 B2
(45) Date of Patent: Jun. 28, 2022

(54) LONG-ACTING PRODRUGS OF RASAGILINE, PREPARING METHODS AND USES THEREOF

(71) Applicant: GUANGZHOU HENOVCOM BIOSCIENCE CO. LTD, Guangzhou (CN)

(72) Inventors: Jiancun Zhang, Guangzhou (CN); Deyao Li, Guangzhou (CN); Yiqian Zhou, Guangzhou (CN); Yiwu Wu, Guangzhou (CN)

(73) Assignee: GUANGZHOU HENOVCOM BIOSCIENCE CO. LTD, Guangzhou (CN)

( * ) Notice: Subject to any disclaimer, the term of this patent is extended or adjusted under 35 U.S.C. 154(b) by 79 days.

(21) Appl. No.: 16/641,802

(22) PCT Filed: Aug. 27, 2018

(86) PCT No.: PCT/CN2018/102494
§ 371 (c)(1),
(2) Date: Feb. 25, 2020

(87) PCT Pub. No.: WO2019/037791
PCT Pub. Date: Feb. 28, 2019

(65) Prior Publication Data
US 2020/0246302 A1    Aug. 6, 2020

(30) Foreign Application Priority Data

Aug. 25, 2017    (CN) .................. 201710742461.X

(51) Int. Cl.
*A61K 31/27* (2006.01)
*A61K 31/4188* (2006.01)
*A61K 31/575* (2006.01)

(52) U.S. Cl.
CPC .......... *A61K 31/27* (2013.01); *A61K 31/4188* (2013.01); *A61K 31/575* (2013.01)

(58) Field of Classification Search
None
See application file for complete search history.

(56) References Cited

U.S. PATENT DOCUMENTS 8,969,337 B2 * 3/2015 Blumberg ................ A61P 9/12
514/220
2015/0210712 A1    7/2015 Blumberg et al.

FOREIGN PATENT DOCUMENTS

| CN | 87101285 A | 8/1988 |
| WO | 9618605 A1 | 6/1996 |

(Continued)

OTHER PUBLICATIONS

Eliel, E. and Wilen, S., "Stereochemistry of Organic Compounds", John Wiley & Sons, Inc., New York, 1994.

(Continued)

*Primary Examiner* — My-Chau T. Tran
(74) *Attorney, Agent, or Firm* — Schmeiser, Olsen & Watts, LLP

(57) ABSTRACT

Provided are a long-acting prodrug of Rasagiline, which has application in the treatment of Central Nervous System diseases such as Parkinson's disease, preparation method and use thereof. The long-acting prodrug of Rasagiline has a structure of formula (I), wherein T is absent, or T is selected from

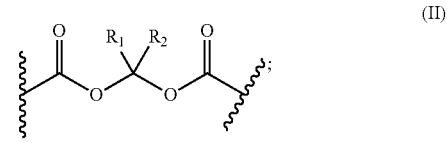

each of $R_1$ and $R_2$ is independently selected from H, D, and alkyl; W is absent, or W is selected from $(CH_2)_n$, wherein n is an integer selected from 1 to 15; X is absent, or X is selected from $(CH_2)_m$, wherein m is an integer selected from 1 to 10; Y is absent, or Y is selected from —C(=O)NH—, —NHC(=O)—; $R_3$ is selected from substituted or unsubstituted $C_1$-$C_{30}$ alkyl, substituted or unsubstituted $C_2$-$C_{30}$ alkenyl, substituted or unsubstituted $C_2$-$C_{30}$ alkynyl, substituted or unsubstituted $C_3$-$C_{30}$ cycloalkyl, cholane aliphatic group, —$R^{3a}$—C(=O)O—$R^{3b}$, —$R^{3a}$—OC(=O)—$R^{3b}$, —$R^{3a}$—C(=O)NH—$R^{3b}$, —$R^{3a}$—NHC(=O)—$R^{3b}$, —$R^{3a}$—S(=O)$_{1-2}$O—$R^{3b}$ and —$R^{3a}$—OS(=O)$_{1-2}$—$R^{3b}$.

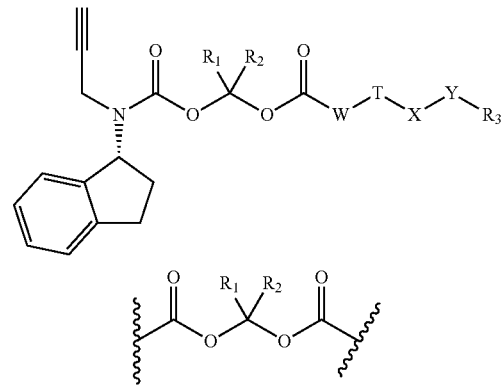

8 Claims, 1 Drawing Sheet

(56) References Cited

FOREIGN PATENT DOCUMENTS

| | | |
|---|---|---|
| WO | 2011084846 A1 | 7/2011 |
| WO | 2013088255 A1 | 6/2013 |

OTHER PUBLICATIONS

International Search Report dated Nov. 28, 2018 for PCT/CN2018/102494, filed Aug. 27, 2018.

* cited by examiner

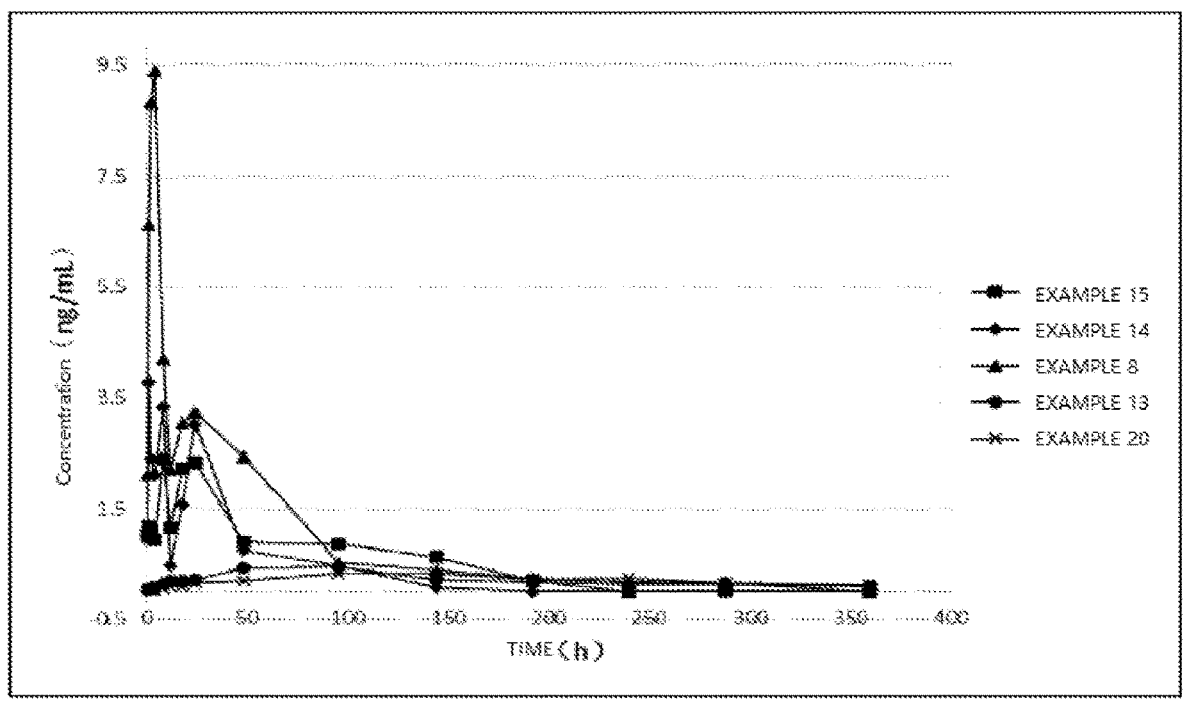

LONG-ACTING PRODRUGS OF RASAGILINE, PREPARING METHODS AND USES THEREOF

CROSS-REFERENCE TO RELATED APPLICATIONS

This application claims priority to PCT Application No. PCT/CN2018/102494, having a filing date of Aug. 27, 2018, which is based on Chinese Application No. 201710742461.X, having a filing date of Aug. 25, 2017, the entire contents both of which are hereby incorporated by reference.

FIELD OF TECHNOLOGY

The following relates to the technical field of medical chemistry, particularly, it relates to a long-acting prodrug of Rasagiline and a preparing method as well as use thereof.

BACKGROUND

Parkinson's disease (PD), also named as paralysis agitans, is a common neurodegenerative disease. It is progressive, multiple with insidious onset etc., and major symptoms may include slowness of movement, muscle rigidity, resting tremor, and posture instability. The morbidity of PD is rare in people aged under 50, but rapidly increases in people aged over 60. It is estimated that there are over 2 million PD patients in China, wherein the morbidity is about 1.7% among people aged over 65, and it is in an increase trend with the process of population aging in China.

Major pathological features of PD are the death of dopaminergic neuron in nigra and degeneration of nigrostriatum pathway. In addition, Lewy bodies exist in the cytosol of residual dopaminergic neurons. The cells in brain that produce dopamine gradually lose their abilities of affecting the nervous system, so that the ability of controlling muscles for patients are getting worse.

Levodopa is dominating in the drug treatment for PD. With an increasing oral dosage and a decreasing administration time of levodopa for treating PD, the efficacy has been weakened and adverse reactions such as on-off phenomena, fluctuations in motor symptoms, and drug tolerance occur more frequently. Monoamine oxidase (MAO-B) in brain is one of key enzymes for dopamine metabolism, and it will generate some free radicals during dopamine catabolism, leading to oxidative stress and causing a neuronal death.

Rasagiline is a second generation of the monoamine oxidase inhibitor and it can block the breakdown of a neurotransmitter dopamine. Compared to Selegiline (a first generation of the monoamine oxidase inhibitor, including selegiline, eldepryl, Jinsiping, and so on), its inhibiting effect is 5-10 times stronger, and it also has an improving effect on patients who suffer weaken efficacy due to long-term administration of dopamine preparations. In addition, compared to selegiline, metabolite of Rasagiline is one type of inactive non-benzedrine substance and has little side-effects. Importantly, such drug can relieve symptoms and there are evidences that such drug has a function of protecting nerve.

Parkinson's disease is a progressive and incurable nervous system disease, and the patients are required to take medicine for a long time. For the Rasagiline, daily administration is necessary. As the Parkinson's disease is mainly in the elderly who have poor memory, there is a great demand for the development of long-acting drugs for Parkinson's disease, and no successful long-acting drug has been publicly reported yet.

WO 2013088255 and US 20150210712 reported a series of prodrug of Rasagiline. It has been found on trial that the compounds reported by the above patents have melting points lower than the room temperature (25° C.), which cannot satisfy the demand of physicochemical properties of long-acting suspensions. Solid particles of such low-melting point compound are prone to fuse together when they are in a long-term storage or after they enter the body, and this makes it difficult to control the release rate of drug in the body, so it is not suitable to be a long-acting drug. Compounds with high melting points and low solubility in water are synthesized through structural improvement, and they are suitable to be long-acting drugs due to uniform release in the body as proved by pharmacokinetic experiments in animal.

SUMMARY

An aspect relates to a long-acting prodrug prepared by modifying a structure of Rasagiline. The prodrug is made into preparations that can be injected intramuscularly, subcutaneously, or intravenously through preparation methods, and form a drug reservoir in the body through an intramuscular, hypodermic, or intravenous injection. The prodrug will be released slowly, sustainably, and steady from the reservoir and converted into Rasagiline, for achieving an effect of long-acting treatment.

It is a first aspect of the present disclosure to provide a long-acting prodrug of Rasagiline or a pharmaceutically acceptable salt, stereoisomer, solvate thereof, and the long-acting prodrug of Rasagiline has a structure of formula I:

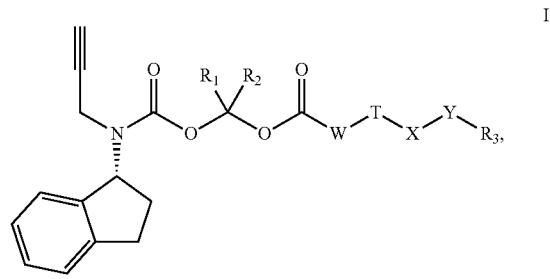

wherein,
T is absent, or T is selected from

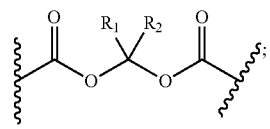

each of $R_1$ and $R_2$ is independently selected from H, D, or $C_{1-4}$ alkyl;
W is absent, or W is selected from $(CH_2)_n$, wherein n is an integer selected from 1 to 15;
X is absent, or X is selected from $(CH_2)_m$, wherein m is an integer selected from 1 to 10;
Y is absent, or Y is selected from C(=O)NH—, or —NHC(=O);

R$_3$ is selected from substituted or unsubstituted C$_1$-C$_{30}$ alkyl, substituted or unsubstituted C$_2$-C$_{30}$ alkenyl, substituted or unsubstituted C$_2$-C$_{30}$ alkynyl, substituted or unsubstituted C$_3$-C$_{10}$ cycloalkyl, cholane aliphatic group, —R$^{3a}$—C(=O)O—R$^{3b}$, —R$^{3a}$—OC(=O)—R$^{3b}$, —R$^{3a}$—C(=O)NH—R$^{3b}$, —R$^{3a}$—NHC(=O)—R$^{3b}$, —R$^{3a}$—S(=O)$_{1-2}$—O—R$^{3b}$ or —R$^{3a}$—OS(=O)$_{1-2}$—R$^{3b}$, wherein each of R$^{3a}$ and R$^{3b}$ is independently selected from substituted or unsubstituted C$_1$-C$_{20}$ alkyl, substituted or unsubstituted C$_2$-C$_{20}$ alkenyl, or substituted or unsubstituted C$_2$-C$_{20}$ alkynyl;

each substituted alkyl comprises 1, 2, 3 or 4 substituents independently selected from oxo (=O), thio (=S), F, Cl, amino, carbonyl, cycloalkyl, aryl, or heteroaryl;

each substituted alkenyl comprises 1, 2, 3 or 4 substituents independently selected from oxo (=O), thio (=S), F, Cl, amino, carbonyl, cycloalkyl, aryl, or heteroaryl;

each substituted alkynyl comprises 1, 2, 3 or 4 substituents independently selected from oxo (=O), thio (=S), F, Cl, amino, carbonyl, cycloalkyl, aryl, or heteroaryl;

each substituted C$_3$-C$_{10}$ cycloalkyl comprises 1, 2, 3 or 4 substituents independently selected from oxo (=O), thio (=S), F, Cl, amino, carbonyl, cycloalkyl, aryl, or heteroaryl;

R$_1$ is H or D, R$_2$ is methyl, H or D; or each of R$_1$ and R$_2$ is independently H, D or methyl.

W, and T are absent; X is absent, or X is selected from (CH$_2$)$_m$, wherein m is an integer selected from 1 to 10; Y is selected from —C(=O)NH, or —NHC(=O); and R$_3$ is selected from aryl (such as naphthyl), substituted C$_1$-C$_6$ alkyl, or linear or branched, saturated or unsaturated C$_7$-C$_{27}$ alkyl.

R$_3$ is —CH=CHR$_4$, wherein R$_4$ is selected from phenyl substituted with one or more groups selected from OH or alkoxy.

R$_3$ is selected from one of the following cholane aliphatic groups:

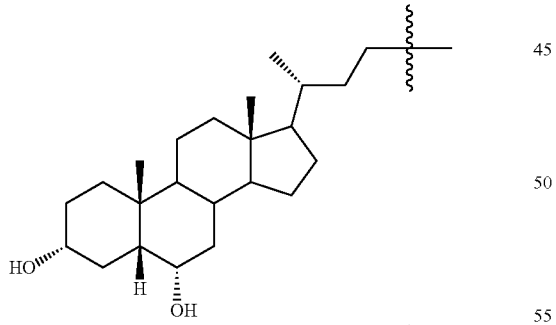

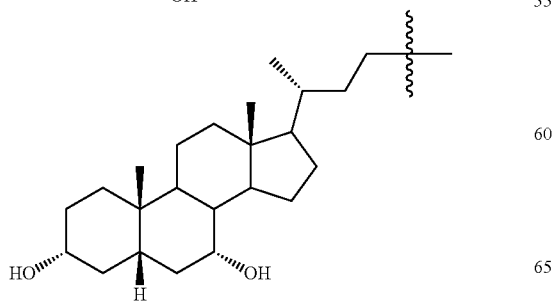

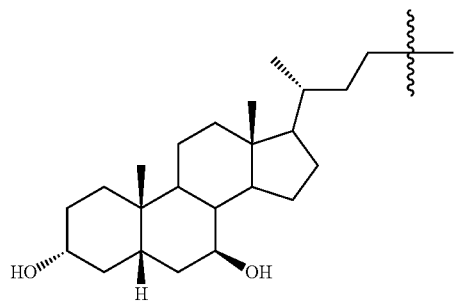

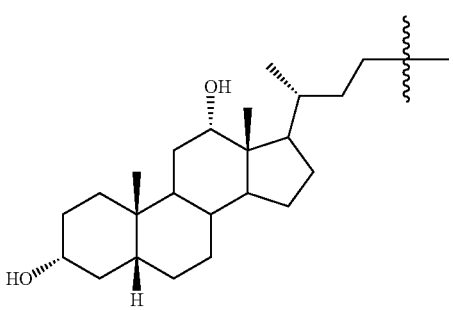

In some examples, the long-acting prodrug of Rasagiline has a structure of formula II:

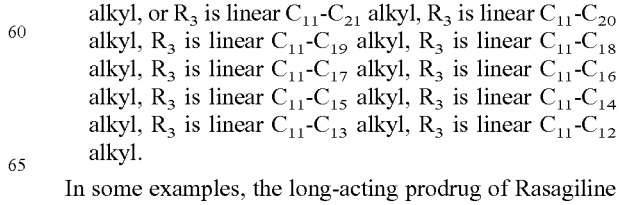

II wherein, r is an integer from 1 to 10; R$_3$ is linear C$_7$-C$_{27}$ alkyl;

wherein r is an integer from 1 to 6, R$_3$ is linear C$_9$-C$_{25}$ alkyl;

wherein r is an integer from 3 to 6, R$_3$ is linear C$_{11}$-C$_{25}$ alkyl, or R$_3$ is linear C$_{11}$-C$_{21}$ alkyl, R$_3$ is linear C$_{11}$-C$_{20}$ alkyl, R$_3$ is linear C$_{11}$-C$_{19}$ alkyl, R$_3$ is linear C$_{11}$-C$_{18}$ alkyl, R$_3$ is linear C$_{11}$-C$_{17}$ alkyl, R$_3$ is linear C$_{11}$-C$_{16}$ alkyl, R$_3$ is linear C$_{11}$-C$_{15}$ alkyl, R$_3$ is linear C$_{11}$-C$_{14}$ alkyl, R$_3$ is linear C$_{11}$-C$_{13}$ alkyl, R$_3$ is linear C$_{11}$-C$_{12}$ alkyl.

In some examples, the long-acting prodrug of Rasagiline is selected from one of the following compounds:

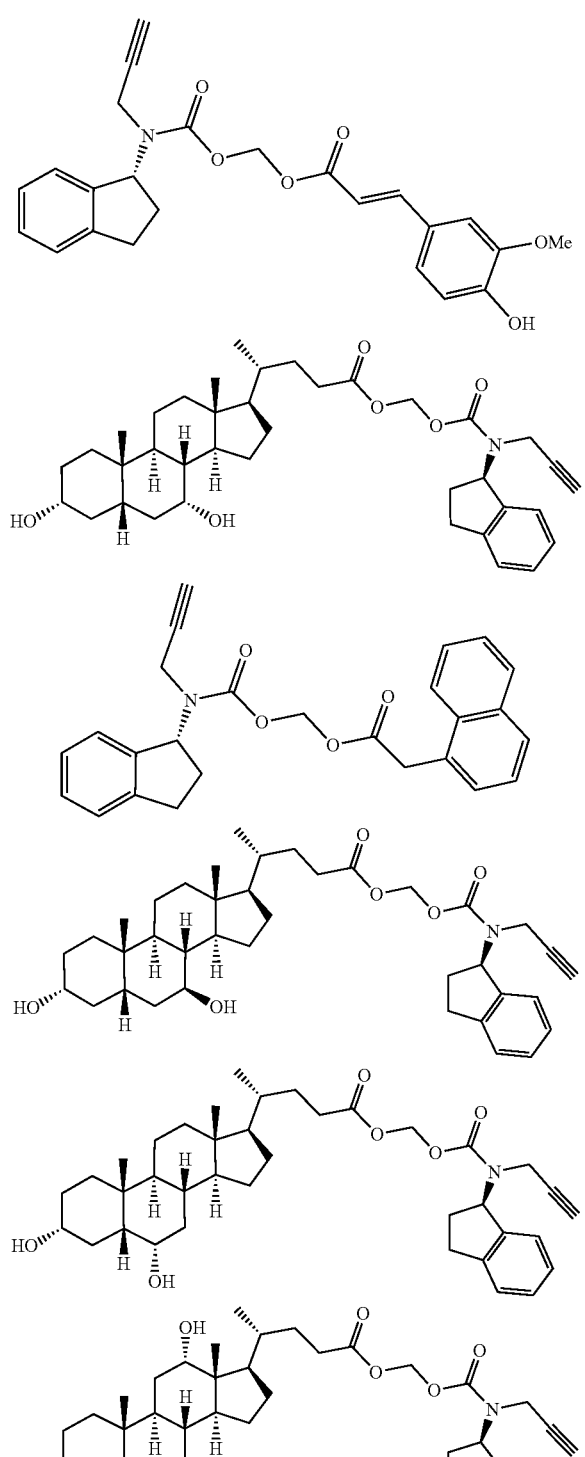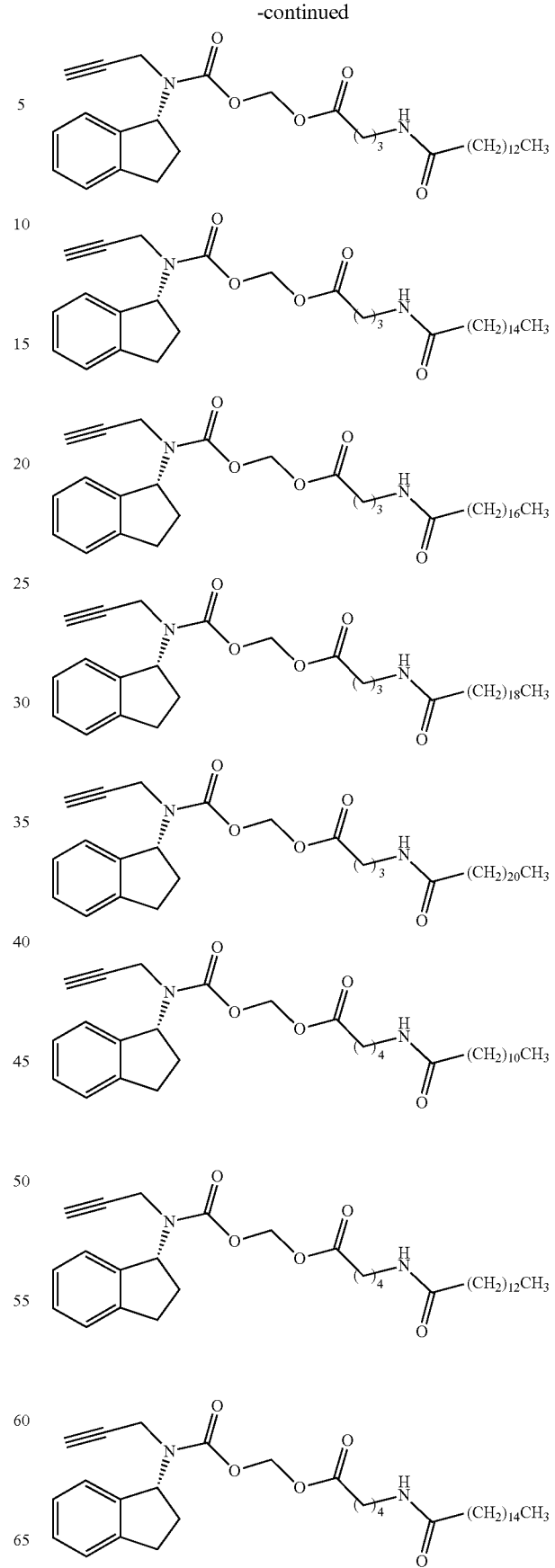

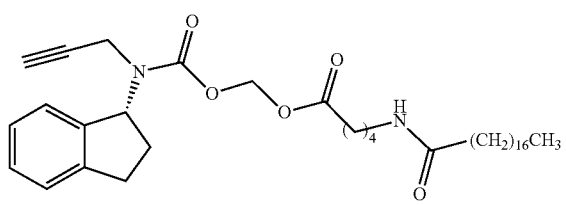
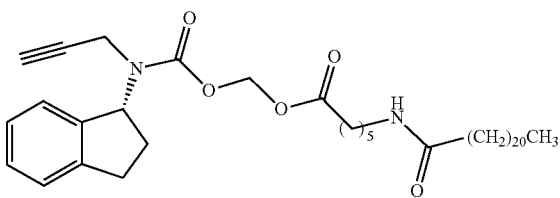

-continued

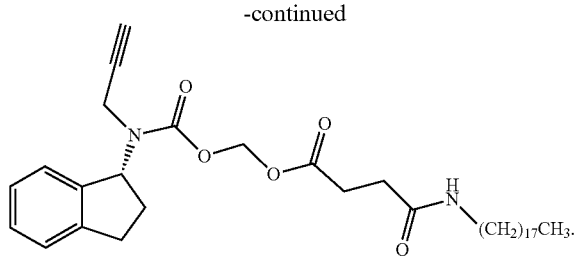

It is another aspect of the present disclosure to provide a method for preparing the above prodrug, the method includes:

Scheme 1

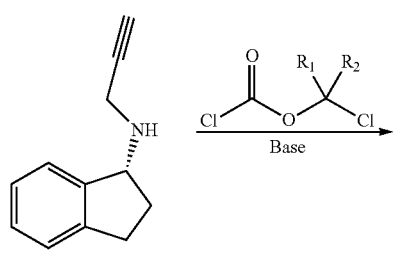

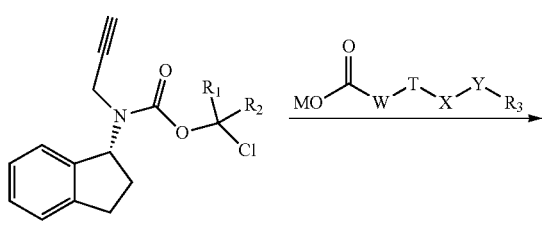

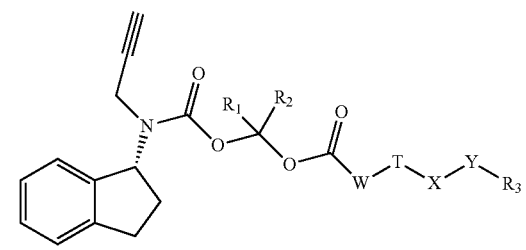

Rasagiline reacts with chloromethyl chloroformate in aprotic solvent in presence of acid-binding agent such as organic base or an inorganic base, to obtain intermediate, which will subsequently react with $MOCOWTXYR_3$ in aprotic solvent (in this reaction, M is a metal ion; and $R_1$, $R_2$, $R_3$, W, T, X, and Y are defined as hereinbefore), or react with $MOCOR_3$ in aprotic solvent in presence of acid-binding agent such as organic base or inorganic base (in this reaction, M is H; and $R_1$, $R_2$, $R_3$, W, T, X, and Y are defined are defined hereinbefore) to obtain the prodrug.

Scheme 2

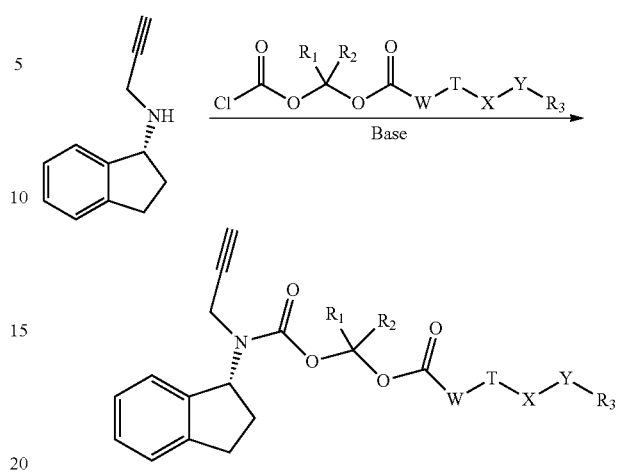

Rasagiline reacts with $ClCOOCR_1R_2OCOWTXYR3$ ($R_1$, $R_2$, $R_3$, W, T, X, and Y are defined as hereinbefore) in aprotic solvent in presence of acid-binding agent such as organic base or inorganic base, to obtain the prodrug.

It is another aspect of the present disclosure to provide a pharmaceutical composition, which comprises above-mentioned compound of formula I or a stereoisomer, solvate and pharmaceutically acceptable carrier or excipient thereof.

The above pharmaceutical composition may be prepared into a form of an injectable suspension injection by taking the prodrug of Rasagiline with low solubility as the active ingredients to combine with the suspended solvent and the pharmaceutically acceptable excipient. The suspension injection forms a drug reservoir in the body from which the prodrug is slowly released and digested into active compounds in the body, thereby a long-acting treatment is achieved.

In one of the examples, the pharmaceutical composition is in a form of freeze-dried powder, suspension or dry suspension. Being in the form of freeze-dried powder or dry suspension has an advantage in great stability during long-term storage, which is beneficial to quality control for the preparations. Being in the form of suspension has an advantage in convenient production. specifically, it is prepared just by grinding and packaging after mixing the prodrug with excipient together, there are less procedures with easy operation, which is advantageous for a large-scale production.

It is another aspect of the present disclosure to provide a use of the foresaid compound of formula I or a stereoisomer, solvate thereof in the preparation of a medicament for preventing and/or treating a central nervous system disease; and a use of the pharmaceutical composition in the preparation of a medicament for preventing and/or treating a central nervous system disease.

The medicament is a long-acting drug.

The central nervous system disease is Parkinson's disease.

It is another aspect of the present disclosure to provide a method of preventing and/or treating a central nervous system disease, the method comprises administering an effective amount of the foresaid prodrug or a stereoisomer, solvate thereof or the foresaid pharmaceutical composition to patients in need; the central nervous system disease is Parkinson's disease.

Unless stated otherwise or there is an obvious conflict in context, the articles "a," "an," and "said" used herein are intended to include "at least one" or "one or more". Therefore, these articles used herein refer to articles of one or more (i.e., at least one) objects. For example, "a component" means one or more components, that is, more than one component may be considered to be applied or used in an example of the disclosure.

The term "comprise" is an open-ended expression, and it includes the content specified in the present disclosure, but does not exclude other aspects.

The term "stereoisomer" refers to compounds having the same chemical structure, but different arrangement of atoms or groups in space. The stereoisomer includes enantiomer, diastereomer, conformer (rotamer), geometric isomer (cis/trans) isomers, atropisomer, etc.

The "enantiomer" refers to two isomers of a compound which are unable to overlap but are mirror images of each other.

The "diastereomer" refers to stereoisomers which have two or more chiral centers and their molecules are not mirror images of each other. The Diastereomer has different physical properties, such as melting points, boiling points, spectral properties, and reactivity. The Diastereomeric mixture can be separated by high resolution analytical operations, for example, electrophoresis and chromatography, such as HPLC.

The stereochemical definitions and rules used in the present disclosure generally follow S. P. Parker, Ed., McGraw-Hill Dictionary of Chemical Terms (1984) McGraw-Hill Book Company, New York; and Eliel, E. and Wilen, S., "*Stereochemistry of Organic Compounds*", John Wiley & Sons, Inc., New York, 1994.

Many organic compounds exist in optically active forms, that is, they have the capacity of rotating a plane of plane-polarized light. When optically active compounds are described, the prefixes D and L or R and S are used to indicate an absolute configuration of the molecule with respect to one or more of its chiral centers. The prefixes d and l or (+) and (−) are symbols referring to the rotation of plane-polarized light caused by a compound, wherein (−) or l indicates that the compound is left-handed, and the compounds prefixed with (+) or d are right-handed. A specific stereoisomer is an enantiomer, and a mixture of such isomers is called an enantiomeric mixture. The mixture of enantiomer at a ratio of 50 to 50 is called a racemic mixture or a racemate, which occurs when there is no stereoselection or stereospecificity in a chemical reaction or process.

Any asymmetric atoms (e.g., carbon, etc.) of a compound disclosed herein can exist in racemic or enantiomerically enriched form, such as (R)-configuration, (S)-configuration, or (R, S)-configuration. In some examples, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)-configuration or (S)-configuration.

According to the selection of starting materials and methods, the compound of the present disclosure may exist in a form of one or a mixture of the possible isomers, such as a mixture of a racemate and a diastereomer (which depends on the amount of asymmetric carbon atoms). Optically active (R)-isomers or (S)-isomers can be prepared by using chiral synthons or chiral reagents, or can be separated by using conventional techniques. If the compound includes a double bond, the substituent may be in the E or Z configuration; if the compound includes a disubstituted cycloalkyl, the substituent of the cycloalkyl may have a cis or trans configuration.

Based on differences in the physicochemical properties of components, the resulting mixture of any stereoisomers can be separated into pure or substantially pure geometric isomers, enantiomers, or diastereomers, for example, by chromatography, and/or fractional crystallization.

Any racemates of resulting product or intermediate can be separated into optical enantiomers by using any methods well-known by one skilled in the art, for example, the resulting diastereoisomeric salt can be separated. Racemic product can also be separated by chiral chromatography, such as high-performance liquid chromatography (HPLC) using a chiral adsorbent.

The term "tautomer" or "tautomeric form" refers to structural isomers with different energies which may be converted into each other by crossing a lower energy barrier. If tautomerization occurs possibly (such as in solution), the chemical equilibrium of the tautomers can be reached. For example, protontautomers (also called as prototropic tautomers) may interconvert, such as ketone-enol isomerization and imine-enylamine isomerization, through proton transfer. Valence tautomers may interconvert through recombination of bonding electrons. A specific example of ketone-enol tautomerism is the tautomerism of tautomers of pentane-2,4-diketone and 4-hydroxypent-3-ene-2-one. Another example of the tautomerism is phenol-ketone tautomerism. A specific example of phenol-ketone tautomerism is the tautomerism of tautomers of pyridin-4-ol and pyridin-4(1H)-one. Unless otherwise indicated, all tautomeric forms of the compounds of the present disclosure are within the scope of the disclosure.

The term "substitute" refers to replacing a hydrogen in specific structure with a specified substituent. If the substitution on the alkyl or cycloalkyl group is not specified to occur on a specific carbon atom it may occurs on any unsaturated carbon atom. When multiple substituents from the same series are selected, they may be the same or different. If the substitution on benzene ring, heteroaromatic ring, or heterocyclic ring of the present disclosure is not specified to occur on a specific atom, it may occurs at any position which are not substituted by other atoms except hydrogen. When multiple substituents from the same series are selected, they may be the same or different. The substituents described herein include, but are not limited to D, F, Cl, Br, I, $N_3$, CN, $NO_2$, OH, SH, $NH_2$, oxygen, sulfur, carboxyl, alkyl, haloalkyl, alkenyl, alkynyl, alkoxy, alkylamino, hydroxyalkyl, cyano-substituted alkyl, cycloalkyl, heterocyclyl, aryl, heteroaryl, etc.

The term "unsubstituted" indicates that the specified group does not have any substituent.

In addition, it should be noted that, unless explicitly stated otherwise, the description ways used in the present disclosure such as "each of . . . is independently selected from . . . " and " . . . are each independently selected from" and " . . . are independently" are interchangeable and should be understood in wide sense. It may mean that the specific options among the same symbols in different groups do not affect each other, it also may mean that the specific options among the same symbols in the same group do not affect each other.

In each part of the description of the present disclosure, the substituents of the compounds disclosed in the present disclosure are disclosed according to the type or scope of the group. In particular, the present disclosure includes each independent subcombination of each member of the type and scope of these groups. For example, the term "$C_{1-30}$ alkyl" specifically refers to independently disclosed methyl, ethyl, $C_3$ alkyl, $C_4$ alkyl, $C_5$ alkyl, $C_6$ alkyl, . . . , $C_{12}$ alkyl, . . . , $C_{20}$ alkyl, . . . , and $C_{30}$ alkyl.

In each part of the description of the present disclosure, linking substituents are described. When it is clear that the structure requires a linking group, the Markush variables listed for the group should be understood as a linking group. For example, if the structure requires a linking group and the Markush group for the variable is defined as "alkyl" or "aryl", it should be understood that the "alkyl" or "aryl" respectively represents an attached alkylene or arylene group.

The term "alkyl" used herein refers to saturated chained alkyl, wherein "chained alkyl" refers to linear or branched alkyl, for example $C_1$-$C_{30}$ alkyl refers to a saturated linear or branched alkyl group having 1-30 carbon atoms, wherein examples of linear alkyl include, but are not limited to methyl, ethyl, n-propyl, butyl, $C_5$ alkyl, $C_6$ alkyl, . . . , $C_{12}$ alkyl, . . . , $C_{20}$ alkyl, . . . , and $C_{30}$ alkyl. Examples of branched alkyl include, but are not limited to isopropyl, tert-butyl, and the like. $C_1$-$C_{27}$ alkyl refers to a saturated linear or branched alkyl having 1-27 carbon atoms, wherein examples of linear alkyl include, but are not limited to methyl, ethyl, n-propyl, butyl, $C_5$ alkyl, $C_6$ alkyl, . . . , $C_{12}$ alkyl, . . . , $C_{20}$ alkyl, . . . , and $C_{27}$ alkyl. Examples of branched alkyl include, but are not limited to isopropyl, tert-butyl, and the like. $C_1$-$C_{25}$ alkyl refers to a saturated linear or branched alkyl having 1 to 25 carbon atoms, wherein examples of linear alkyl include, but are not limited to methyl, ethyl, n-propyl, butyl, $C_5$ alkyl, $C_6$ alkyl, . . . , $C_{12}$ alkyl, . . . , $C_{20}$ alkyl, . . . , and $C_{25}$ alkyl. Examples of branched alkyl include, but are not limited to isopropyl, tert-butyl, and the like. $C_1$-$C_{20}$ alkyl refers to a saturated linear or branched alkyl group having 1 to 20 carbon atoms, wherein examples of linear alkyl include, but are not limited to methyl, ethyl, n-propyl, butyl, $C_5$ alkyl, $C_6$ alkyl, . . . , $C_{12}$ alkyl, . . . , and $C_{20}$ alkyl. Examples of branched alkyl include, but are not limited to isopropyl, tert-butyl, and the like. $C_1$-$C_{15}$ alkyl refers to a saturated linear or branched alkyl having 1 to 15 carbon atoms, wherein examples of linear alkyl include but are not limited to methyl, ethyl, n-propyl, butyl, $C_5$ alkyl, $C_6$ alkyl, . . . , $C_{12}$ alkyl, . . . , and $C_{15}$ alkyl. Examples of branched alkyl include, but are not limited to isopropyl, tert-butyl, and the like. $C_1$-$C_{12}$ alkyl refers to a saturated linear or branched alkyl group having 1 to 12 carbon atoms, examples of the linear alkyl include, but are not limited to methyl, ethyl, n-propyl, butyl, $C_5$ alkyl, $C_6$ alkyl, . . . , and $C_{12}$. Examples of branched alkyl include, but are not limited to isopropyl, tert-butyl, and the like. The alkyl group may be optionally substituted with one or more of substituents described herein.

The "alkenyl" refers to a linear or branched group with a double bond. For example, $C_2$-$C_{30}$ alkenyl refers to a linear or branched group with a double bond having 2-30 carbon atoms, and examples include but are not limited to vinyl, propenyl, butenyl, pentenyl, $C_6$ alkenyl, . . . , $C_{12}$ alkenyl, . . . and $C_{30}$ alkenyl. The alkenyl group may be optionally substituted with one or more of substituents described herein.

The "alkynyl" refers to a linear or branched group with a triple bond. For example, $C_2$-$C_{30}$ alkenyl refers to a linear or branched group with a triple bond having 2-30 carbon atoms, and examples include but are not limited to ethynyl, propynyl, butynyl, pentynyl, $C_6$ alkynyl, . . . , $C_{12}$ alkynyl, . . . and $C_{30}$ alkynyl. The alkynyl group may be optionally substituted with one or more of substituents described herein.

The term "alkoxy" refers to a linear or branched alkyl with an oxygen atom at the end, and examples include but are not limited to methoxy, ethoxy, n-propoxy, isopropoxy, n-butoxy and the like.

The term "cycloalkyl" refers to an alkyl with a cyclic structure. For example, $C_3$-$C_{10}$ cyclic alkyl refers to a saturated or unsaturated alkyl with a cyclic structure having 3-10 carbon atoms, wherein examples of saturated cyclic alkyl group include, but are not limited to cyclopropyl, cyclopentyl, cyclohexyl, . . . , $C_{10}$ cycloalkyl, and the like, and examples of the unsaturated cyclic alkyl include, but are not limited to cyclopentene, and the like. The cycloalkyl group may be optionally substituted with one or more of substituents described herein.

The term "heteroaryl" refers to an aromatic ring group in which at least one carbon atom of ring is substituted with a heteroatom selected from nitrogen, oxygen, and sulfur, it may be a 5-7 membered monocyclic heteroaryl or a 7-12 membered bicyclic heteroaryl. Examples include, but are not limited to pyridyl, pyrimidinyl, pyridazinyl, pyrazinyl, furyl, thienyl, thiazolyl, oxazolyl, isoxazolyl, isothiazolyl, imidazolyl, pyrazolyl, triazolyl, tetrazolyl, etc. The heteroaryl group may be optionally substituted with one or more of substituents described herein.

The term "carbonyl" refers to —(C=O)—, no matter it is used individually or with other terms, such as "aminocarbonyl" or "acyloxy".

The term "unsaturated" used herein means that a group contains one or more degrees of unsaturation.

The term "heteroatom" refers to O, S, N, P, and Si, including the forms of any oxidation states of N, S and P; primary ammonium salts, secondary ammonium salts, tertiary ammonium salts, and quaternary ammonium salts; or a hydrogen coupled to nitrogen atom in a heterocyclic ring being substituted.

The term "prodrug" used herein refers to a compound which is converted into a compound of formula I-XXI in the body. Such convention is affected by hydrolysis of prodrug in the blood or the prodrug being converted into the parent structure in the blood or tissues in presence of enzymes.

The term "solvate" used herein describes a molecule complex comprising a compound of the present disclosure and one or more pharmaceutically acceptable solvent molecules such as ethanol in stoichiometric amount. The term "hydrate" is used when the solvent is water.

Compared to the conventional art, the present disclosure has the following benefits:

The prodrug of Rasagiline of the present disclosure has a high melting point and low solubility, and it can be made into a suspension and form a drug reservoir in the body by intramuscular injection or subcutaneous injection, prolonging the release time of the drug in the body, and achieving an effect of long-acting treatment.

BRIEF DESCRIPTION OF DRAWINGS

Some of the embodiments will be described in detail, with reference to the following FIGURES, wherein like designations denote like members, wherein:

FIG. 1 depicts a drug-time curve of Rasagiline after it was intramuscularly injected into a beagle.

DETAILED DESCRIPTION

The present disclosure will be further described by the following examples. However, the examples are not intended to limit the protection scope of the present disclosure.

Example 1 Preparation of methyl ((Rasagiline-N-formyl)oxy)-palmitate (Referring to International patent application WO2013088255)

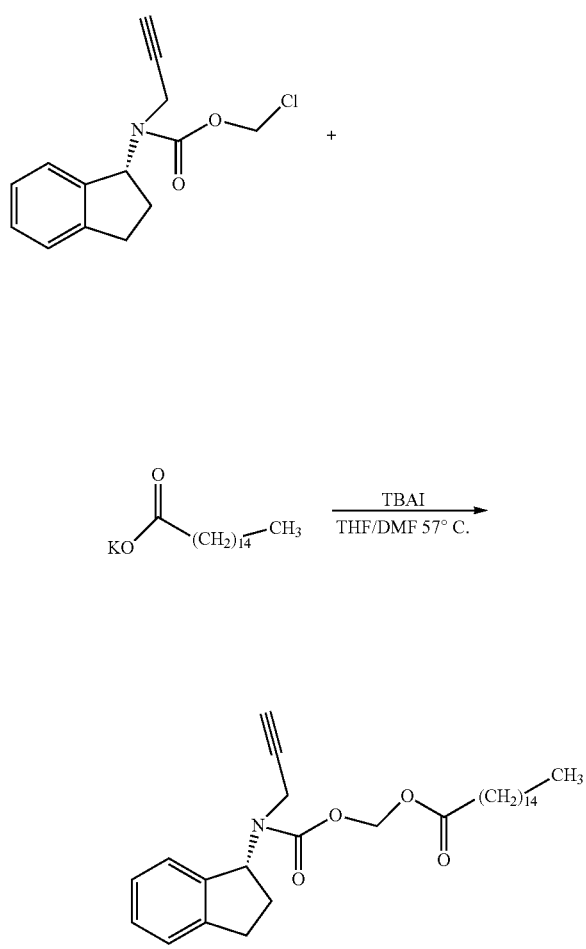

1.0 g of Rasagiline-N-chloromethyl formate and 0.3 g of TBAI were dissolved in THF/DMF (5+4 mL), and then 1.5 g of potassium palmitate was added to obtain a mixture. The mixture was heated at 57° C. overnight under the protection of argon. After the reaction was stopped, THF was removed through rotary evaporation. 30 ml of isopropyl ether was added and stirred for 10 minutes. After a filtering, a filtrate was successively washed with water (15 mL filtrate) and saturated NaHCO$_3$. Then the washed filtrate was dried by anhydrous sodium sulfate and concentrated. The concentrate was purified through silica gel column chromatography (PE:EA=20:1 to 10:1), so as to obtain 0.76 g of a viscous product, with a yield of 41.53%.

$^1$H-NMR(CDCl$_3$, 400 MHz) δ 7.26 (m, 2H), 7.19 (m, 2H), 5.87 (m, 2.5H), 5.78 (m, 0.5H), 4.17 (d, J=14.0 Hz, 0.5H), 4.02 (d, J=14.0 Hz, 0.5H), 3.62 (d, J=14.0 Hz, 0.5H), 3.52 (d, J=14.0 Hz, 0.5H), 3.06 (m, 1H), 2.86 (m, 1H), 2.47 (m, 1H), 2.36 (m, 2H), 2.24 (m, 1H), 2.21 (s, 0.5H), 2.15 (s, 0.5H), 1.64 (m, 2H), 1.28 (m, 24H), 0.88 (t, J=5.2 Hz, 3H).

ESI-MS, C$_{30}$H$_{45}$NO$_4$ (483.3), a measured value of 506.4 [M+Na]$^-$.

Example 2 Preparation of methyl ((Rasagiline-N-formyl)oxy)-naphthalene Acetate

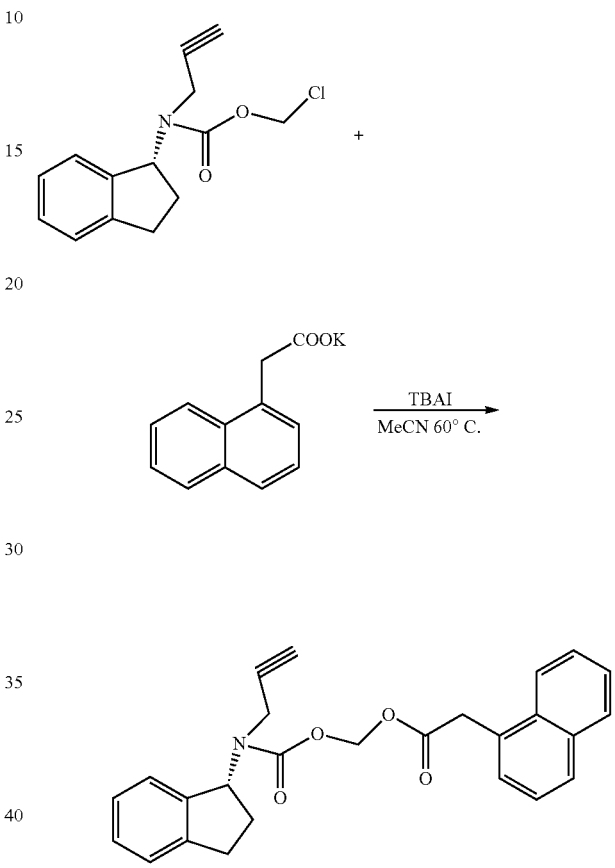

0.9 g of Rasagiline-N-chloromethyl formate and 0.25 g of TBAI were dissolved in 15 mL of acetonitrile, and 0.92 g of potassium naphthalene acetate was added to obtain a mixture. The mixture was heated at 60° C. for 5 hours under the protection of argon. After the reaction was stopped, the solvent was removed through rotary evaporation, and then 20 mL of ethyl acetate was added to for dissolution. Then the mixture was successively washed with saturated NaHCO$_3$ (10 mL×3) and saturated NaCl (10 mL), dried by anhydrous Na$_2$SO$_4$. After a filtration and rotation to dryness, 1.38 g of a brown pulpy crude product was obtained. The crude product was recrystallized through methanol to obtain 0.65 g of a white solid powder, that is a pure methyl ((Rasagiline-N-formyl)oxy)-naphthalene acetate.

$^1$HNMR(CDCl$_3$, 400 MHz) δ 8.01 (dd, J=14.8, 8.4 Hz, 1H), 7.84 (m, 2H), 7.5 (m, 4H), 7.22 (m, 3H), 7.09 (m, 1H), 5.90 (m, 1.5H), 5.82 (dd, J=14.8, 6.0 Hz 1H), 5.54 (t, J=8.0 Hz, 0.5H), 4.16 (s, 1.07H), 4.13 (s, 0.93H), 4.08 (d, J=18.4 Hz, 0.51H), 3.87 (d, J=18.4 Hz, 0.54H), 3.53 (d, J=18.4.6 Hz, 0.49H), 3.39 (d, J=18.4 Hz, 1H), 3.03 (m, 1H), 2.87 (m, 1H), 2.82 (m, 1H), 2.76 (m, 1H), 2.46 (m, 0.5H), 2.26 (m, 0.5H), 2.15 (m, 1.5H), 1.93 (s, 0.5H).

ESI-MS, C$_{26}$H$_{23}$NO$_4$ (413.1), a measured value of 436.1 [M+Na]$^+$.

Example 3 Preparation of methyl ((Rasagiline-N-formyl)oxy)-stearate (Referring to International patent application WO2013088255)

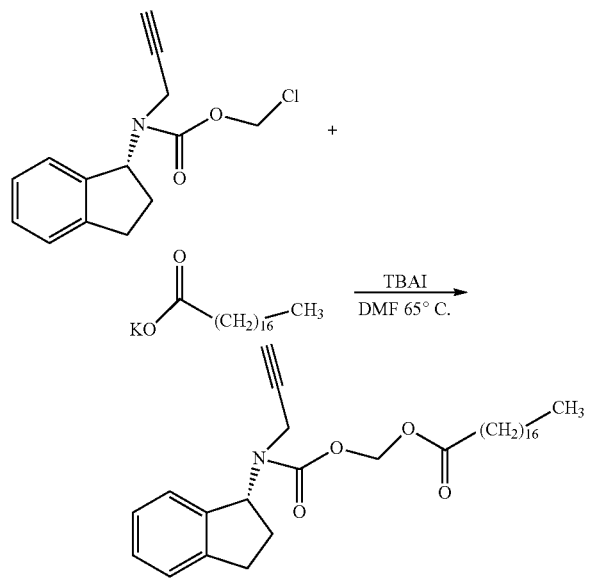

2.0 g of Rasagiline-N-chloromethyl formate and 0.56 g of TBAI were dissolved in 40 mL of DMF, and 3.2 g of potassium stearate was added to obtain a mixture. The mixture was heated at 65° C. overnight under the protection of argon. After the reaction was stopped, 80 ml of water was added, and then 80 mL of isopropyl ether was added for extraction. The extract was successively washed with saturated NaHCO$_3$ (30 mL×2) and saturated NaCl (30 mL), and dried by anhydrous sodium sulfate. After a filtration and rotation to dryness, 4.32 g of a crude product was obtained. The crude product was purified by silica gel column chromatography (PE:EA=10:1), so as to obtain 3 g of a brown pulpy product with a yield of 51.55%.

$^1$HNMR (CDCl$_3$, 400 MHz) δ 7.25 (m, 2H), 7.19 (m, 2H), 5.87 (m, 2.5H), 5.66 (m, 0.5H), 4.12 (d, J=17.6 Hz, 0.5H), 3.98 (d, J=17.6 Hz, 0.5H), 3.57 (d, J=17.6 Hz, 0.5H), 3.47 (d, J=17.6 Hz, 0.5H), 3.06 (m, 1H), 2.85 (m, 1H), 2.46 (m, 1H), 2.37 (m, 2H), 2.24 (m, 1H), 2.16 (s, 0.5H), 2.10 (s, 0.5H), 1.64 (m, 2H), 1.26 (m, 28H), 0.88 (t, J=6.4 Hz, 3H).

ESI-MS, C$_{32}$H$_{49}$NO$_4$ (511.37), a measured value of 534.2 [M+Na]$^+$.

Example 4 Preparation of methyl ((Rasagiline-N-formyl)oxy)-pivalate

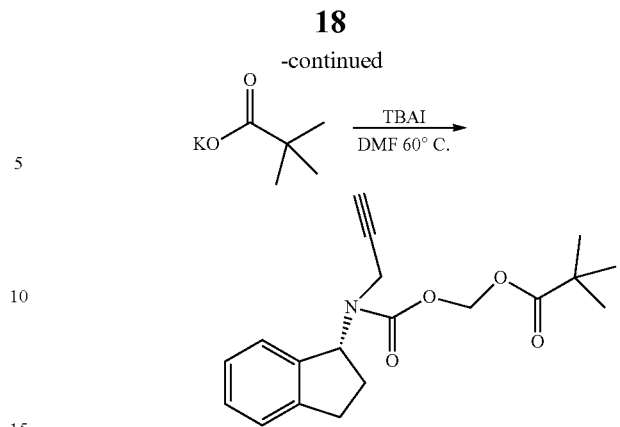

2.0 g of Rasagiline-N-chloromethyl formate and 0.56 g of TBAI were dissolved in 30 mL of DMF, and then 1.38 g of potassium pivalate was added to obtain a mixture. The mixture was heated at 60° C. overnight under a protection of argon. After the reaction was stopped, 80 ml of water was added, and then 80 mL of isopropyl ether was added for extraction. The extract was successively washed with saturated NaHCO$_3$ (30 mL) and saturated NaCl (30 mL), and dried by anhydrous sodium sulfate. After a filtration and rotation to dryness, a crude product was obtained. The crude product was purified through silica gel column chromatography (PE:EA=15:1) to obtain 1.89 g of a light yellow pulpy product, with a yield of 75.60%.

$^1$HNMR (CDCl$_3$, 400 MHz) δ 7.25 (m, 2H), 7.19 (m, 1H), 7.16 (m, 1H), 5.85 (m, 2.5H), 5.84 (m, 0.5H), 4.13 (d, J=14.4 Hz, 0.5H), 3.99 (d, J=14.4 Hz, 0.5H), 3.56 (d, J=14.4 Hz, 0.5H), 3.47 (d, J=14.4 Hz, 0.5H), 3.06 (m, 1H), 2.87 (m, 1H), 2.46 (m, 1H), 2.24 (m, 1H), 2.16 (s, 0.5H), 2.11 (s, 0.5H), 1.23 (m, 9H).

ESI-MS, C$_{19}$H$_{23}$NO$_4$ (329.16), a measured value of 330.1 [M+H]$^+$.

Example 5 Preparation of methyl ((Rasagiline-N-formyl)oxy)-icosanoate (Referring to International patent application WO2013088255)

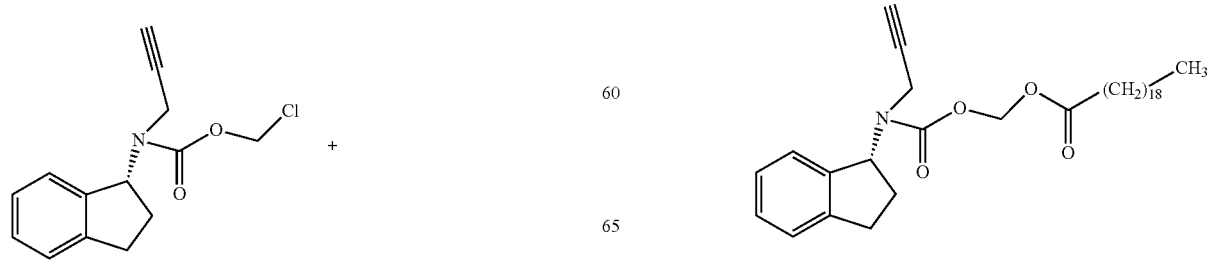

1.73 g of Rasagiline-N-chloromethyl formate and 0.50 g of TBAI were dissolved in 30 mL of DMF, and 3.0 g of potassium icosanoate was added to obtain a mixture. The mixture was heated at 60° C. overnight under the protection of argon. After the reaction was stopped, 80 ml of water was added, and then 80 mL of isopropyl ether was added for extraction. The extract was successively washed with saturated $NaHCO_3$ (30 mL) and saturated NaCl (30 mL), and dried by anhydrous sodium sulfate. After a filtration and rotation to dryness, 1.55 g of a light yellow semisolid product was obtained through silica gel column chromatography (PE:EA=15:1), with a yield of 43.78%.

$^1$HNMR($CDCl_3$, 400 MHz) δ 7.25(m, 2H), 7.18 (m, 2H), 5.85 (m, 2.5H), 5.78 (m, 0.5H), 4.12 (d, J=17.6 Hz, 0.5H), 3.98 (d, J=17.6 Hz, 0.5H), 3.57 (d, J=17.6 Hz, 0.5H), 3.47 (d, J=17.6 Hz, 0.5H), 3.06 (m, 1H), 2.86 (m, 1H), 2.47 (m, 1H), 2.37 (m, 2H), 2.24 (m, 1H), 2.16 (s, 0.5H), 2.10 (s, 0.5H), 1.64 (m, 2H), 1.26 (m, 32H), 0.88 (t, J=6.8 Hz, 3H).

ESI-MS, $C_{34}H_{53}NO_4$ (539.4), a measured value of 562.3 [M+Na]$^+$.

Example 6 Preparation of methyl ((Rasagiline-N-formyl)oxy)-hyodeoxycholate

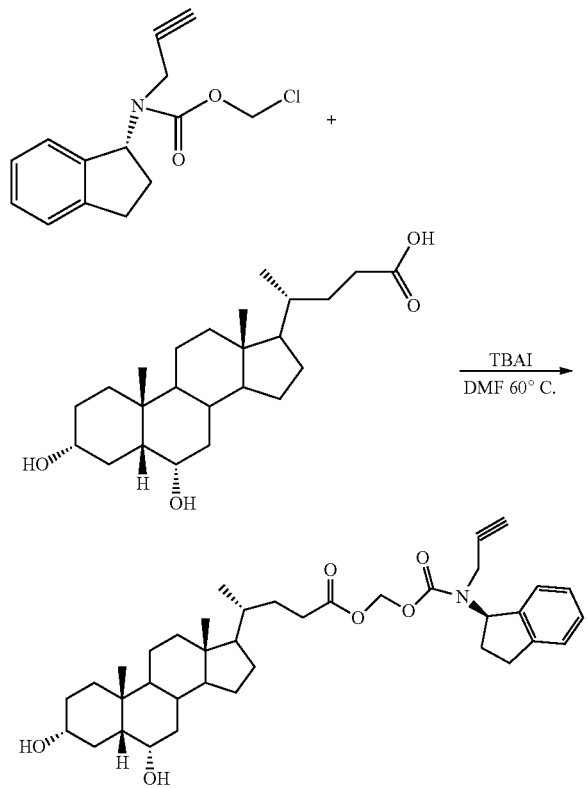

1.48 g of Rasagiline-N-chloromethyl formate and 0.44 g of TBAI were dissolved in 8 mL of DMF, and 2.3 g of hyodeoxycholic acid was added to obtain a mixture The mixture was heated at 60° C. overnight under the protection of argon. After the reaction was stopped, 30 ml of saturated NaCl and 40 mL of ethyl acetate were added and stirred well. An organic phase was separated, and successively washed with saturated NaCl (30 mL), water (30 mL, stirring), saturated $NaHCO_3$ (30 mL), and saturated NaCl (30 mL), followed by being dried by anhydrous sodium sulfate. After a filtration and rotation to dryness, 1.4 g of a white foamed product was obtained through silica gel column chromatography (PE:EA=3:1 organic phase), with a yield of 40.23%.

$^1$H-NMR($CDCl_3$, 400 MHz) δ 7.25 (m, 2H), 7.17 (m, 2H), 5.85 (m, 1.6H), 5.78 (s, 1H), 5.66 (m, 0.4H), 4.12 (d, J=17.6 Hz, 0.53H), 4.05 (m, 1H), 3.98 (d, J=17.6 Hz, 0.47H), 3.62 (m, 1H), 3.57 (d, J=17.6 Hz, 0.47H), 3.48 (d, J=17.6 Hz, 0.53H), 3.07 (m, 1H), 2.87 (m, 1H), 2.42 (m, 2H), 2.35 (s, 1H), 2.27 (m, 1H), 2.16 (s, 0.47H), 2.11 (s, 0.53H), 1.86 (m, 6H), 1.65 (m, 2H), 1.38 (m, 9H), 1.12 (m, 10H), 0.91 (m, 6H), 0.63 (s, 3H).

ESI-MS, $C_{38}H_{53}NO_6$ (619.39), a measured value of 642.2 [M+Na]$^+$.

Example 7 Preparation of methyl ((Rasagiline-N-formyl)oxy)-biotin methyl ester

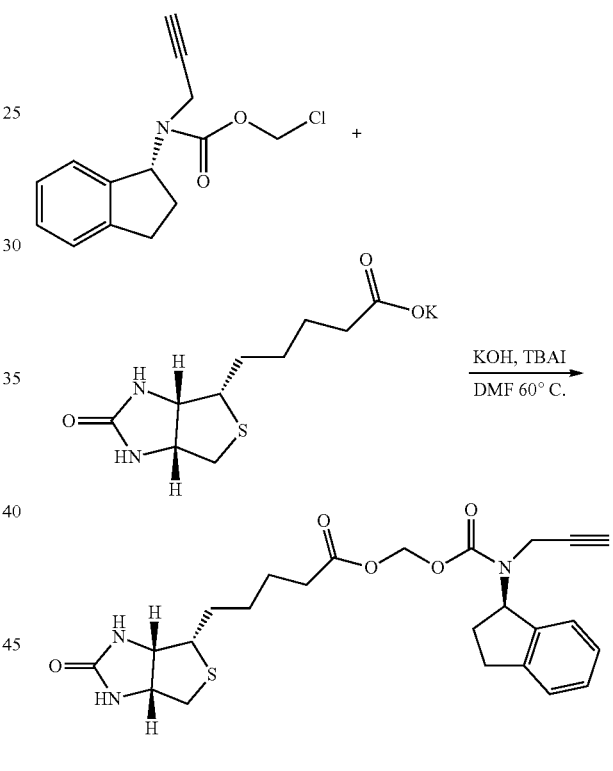

1.5 g of Rasagiline-N-chloromethyl formate, 2.0 g of biotin methyl potassium salt and 0.44 g of TBAI were dissolved in DMF, and they were kept reacting at 60° C. overnight under the protection of argon. After the reaction was stopped, 30 ml of saturated NaCl and 40 mL of ethyl acetate were added and stirred well. An organic phase was separated, and was successively washed with saturated NaCl (30 mL×3), water (30 mL×2), saturated $NaHCO_3$ (30 mL) and saturated NaCl (30 mL), followed by being dried by anhydrous sodium sulfate. After a filtration and rotation to dryness, 1.9 g of a white solid powder product was obtained through silica gel column chromatography (EA-EA/MeOH=10:1), with a yield of 70.90%.

$^1$H-NMR($CDCl_3$, 400 MHz), δ 7.25 (m, 2H), 7.18 (m, 2H), 5.89 (s, 1H), 5.81 (m, 3H), 5.05 (s, 1H), 4.52 (m, 1H), 4.33 (m, 1H), 4.13 (d, J=18.0 Hz, 0.5H), 4.01 (d, J=18.0 Hz, 0.5H), 3.60 (d, J=18.0 Hz, 0.5H), 3.50 (d, J=18.0 Hz, 0.5H), 3.17 (m, 2H), 3.09 (m, 1H), 2.90 (m, 2H), 2.78 (s, 0.6H), 2.75 (s, 0.4H), 2.44 (m, 3H), 2.27 (m, 1H), 1.72 (m, 2H), 1.49 (m, 2H), 1.18 (m, 2H).

Example 8 Preparation of methyl ((Rasagiline-N-formyl)oxy)-ferulate

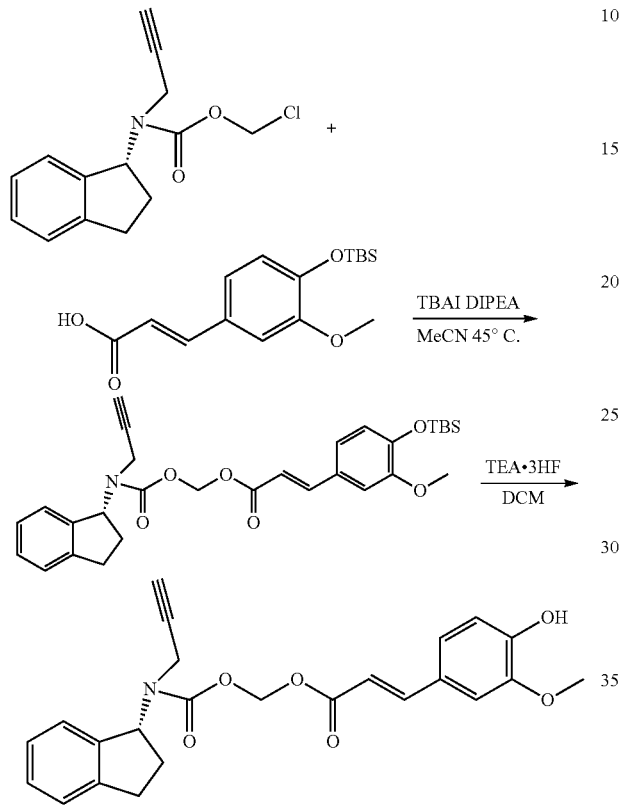

3.8 g of ferulic acid protected by TBS was added to a mixed solution of 3.0 g of Rasagiline-N-chloromethyl formate, 2.0 g of DIPEA and 0.9 g of TBAI in acetonitrile, following by being stirred at 45° C. overnight. After the reaction liquid was removed through rotation to dryness, the resulting concentrate was added with PE (60 mL), EA (20 mL), and water (50 mL), and stirred to layer. An organic phase was separated, and successively washed with saturated $NaHCO_3$ (30 mL), 0.05 mol/L diluted HCl (40 mL), water (40 mL), saturated NaCl (40 mL), and dried by anhydrous sodium sulfate. After a filtration and rotation to dryness, 15 mL of DCM was added for dissolution, and then, 1.68 g of triethylamine trihydrofluoride was added for deprotection. Then the reaction liquid was rotated to dryness, and EA (60 mL) was added for dissolution, a mixture was obtained. The mixture was successively washed with water (30 mL, in succession) and saturated NaCl (30 mL), and dried by anhydrous sodium sulfate. After a filtration and rotation to dryness, 30 mL of methyl tert-butyl ether was added to the concentrate and beat, and a white solid powder was obtained through silica gel column chromatography (DCM). Methyl tert-butyl ether was used to beat twice, and 1.16 g of a white solid powder product was obtained.

1H-NMR (CDCl3, 400 MHz), δ 7.74 (m, 1H), 7.25 (m, 2H), 7.19 (m, 2H), 7.12 (dd, J=8.0, 2.0 Hz, 1H), 7.07 (m, 1H), 6.96 (s, 0.52H) 6.95 (s, 0.48H), 6.34 (dd, J=16.0, 11.2 Hz, 1H), 6.00 (m, 3H), 5.88 (t, J=8.0 Hz, 0.52H), 5.72 (t, J=8.0 Hz, 0.48H), 4.15 (dd, J=18.0, 2.8 Hz, 0.48H), 4.03 (dd, J=18.0, 2.8 Hz, 0.52H), 3.96 (s, 3H), 3.60 (dd, J=18.0, 2.8 Hz, 0.48H), 3.51 (dd, J=18.0, 2.8 Hz, 0.52H), 3.09 (m, 1H), 2.88 (m, 1H), 2.49 (m, 1H), 2.27 (m, 1H), 2.19 (s, 0.48H), 2.12 (s, 0.52H).

ESI-MS, $C_{24}H_{23}NO_6$ (421.15), a measured value of 422.1 $[M+H]^+$.

Example 9 Preparation of methyl ((Rasagiline-N-formyl)oxy)-chenodeoxycholate

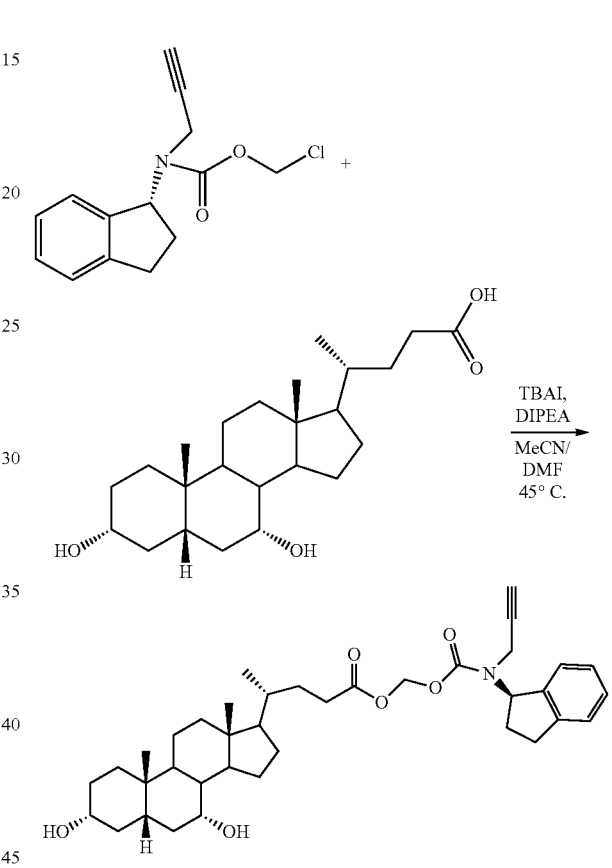

1.14 g of DIPEA was added to a mixed solution of 1.7 g of Rasagiline-N-chloromethyl formate, 2.7 g of chenodeoxycholic acid and 0.5 g of TBAI in acetonitrile and DMF (20+5 ml), followed by being stirred at 45° C. overnight. After the reaction liquid was rotated to dryness and added with EA for dissolution, a mixture was obtained. The mixture was successively washed with saturated NaCl (30 mL×2), 0.05 mol/L diluted HCl (30 mL×2), water (30 mL), saturated $NaHCO_3$ (30 mL) and saturated NaCl (30 mL), and dried by anhydrous sodium sulfate. After a filtration and rotation to dryness, 1.21 g of a white solid product was obtained through silica gel column chromatography (PE/EA=3:1), with a yield of 30.25%.

1H-NMR(CDCl3, 400 MHz) δ 7.25 (m, 2H), 7.17 (m, 2H), 5.85 (m, 2.24H), 5.78 (s, 0.76H), 4.12 (d, J=17.6 Hz, 0.5H), 3.98 (d, J=17.6 Hz, 0.5H), 3.85 (m, 1H), 3.57 (d, J=17.6 Hz, 0.5H), 3.47 (m, 1.5H), 3.06 (m, 1H), 2.86 (m, 1H), 2.43 (m, 2H), 2.35 (s, 1H), 2.28 (m, 2H), 2.18 (s, 0.5H), 2.11 (s, 0.5H), 1.98 (m, 2H), 1.82 (m, 4H), 1.70 (m, 2H), 1.40 (m, 12H), 1.15 (m, 6H), 0.99 (m, 2H), 0.92 (m, 6H), 0.66 (m, 3H).

ESI-MS, $C_{38}H_{53}NO_6$ (619.39), a measured value of 642.2 [M+Na]$^+$.

Example 10 Preparation of methyl ((Rasagiline-N-formyl)oxy)-ursodesoxycholate

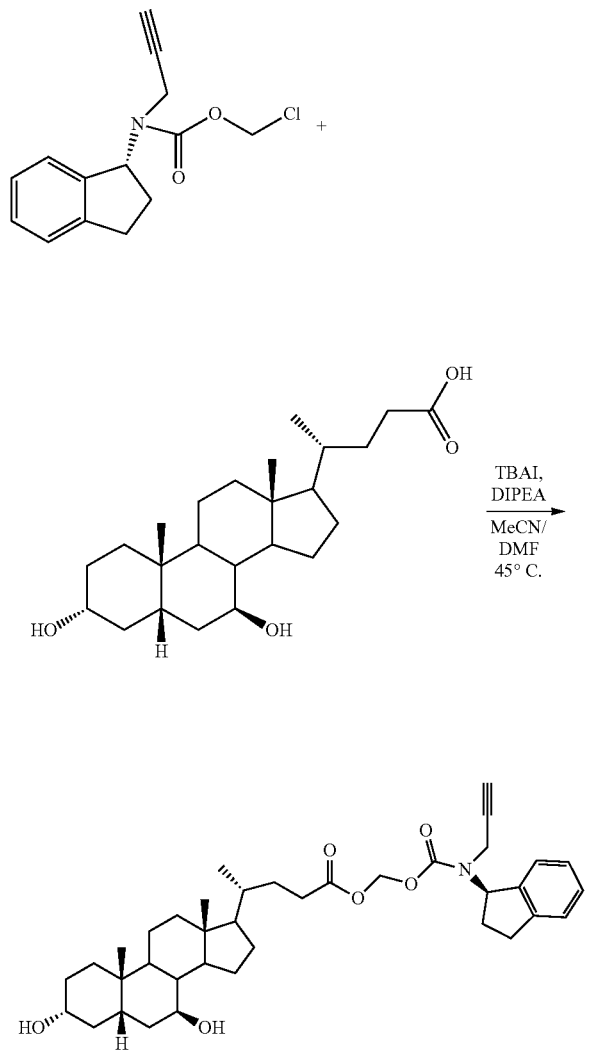

1.5 g of Rasagiline-N-chloromethyl formate was added to a mixed solution of 1.0 g of DIPEA, 2.8 g of ursodesoxycholic acid and 0.44 g of TBAI in acetonitrile and DMF (20/5 ml), followed by being stirred at 45° C. overnight. After the reaction liquid was rotated to dryness and added with EA for dissolution, a mixture was obtained. The mixture was successively washed with saturated NaCl (30 mL×2), 0.05 mol/L diluted HCl (30 mL×2), water (30 mL), saturated NaHCO$_3$ (30 mL) and saturated NaCl (30 mL), and dried by anhydrous sodium sulfate. After a filtration and rotation to dryness, 1.51 g of a white solid product was obtained through silica gel column chromatography (PE/EA=3:1 to 1:1), with a yield of 42.78%.

$^1$H-NMR(CDCl$_3$, 400 MHz), δ 7.25 (m, 2H), 7.17 (m, 2H), 5.84 (m, 2H), 5.77 (s, 1H), 4.12 (d, J=18.0 Hz, 0.55H), 4.05 (m, 1H), 3.98 (d, J=18.0 Hz, 0.45H), 3.62 (m, 1H), 3.57 (d, J=18.0 Hz, 0.55H), 3.48 (d, J=18.0 Hz, 0.55H), 3.07 (m, 1H), 2.86 (m, 1H), 2.42 (m, 2H), 2.35 (s, 1H), 2.26 (m, 2H), 2.16 (s, 0.45H), 2.10 (s, 0.55H), 1.87 (m, 6H), 1.67 (m, 3H), 1.37 (m, 10H), 1.13 (m, 8H), 0.91 (m, 6H), 0.63 (m, 3H).

ESI-MS, $C_{38}H_{53}NO_6$ (619.39), a measured value of 642.2 [M+Na]$^+$.

Example 11 Preparation of methyl ((Rasagiline-N-formyl)oxy)-deoxycholate

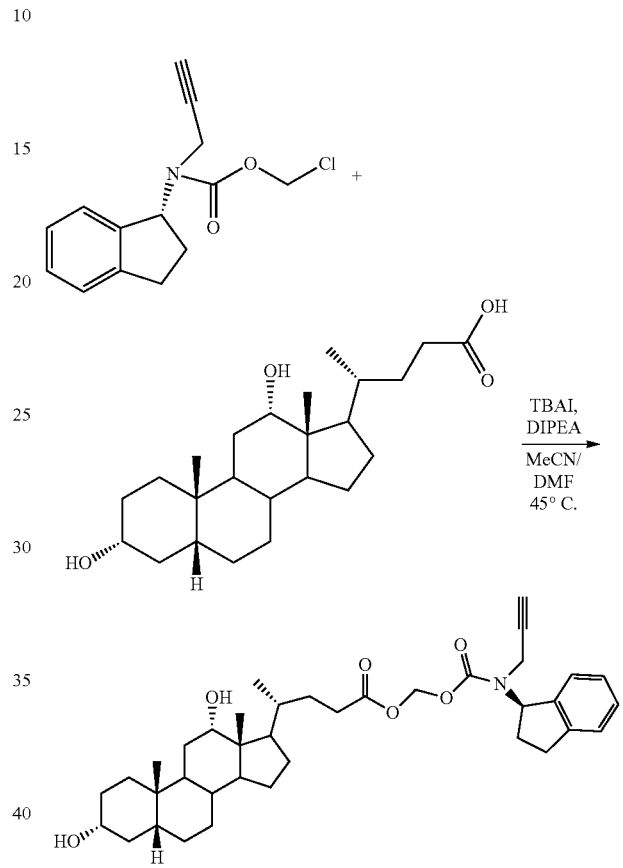

1.5 g of Rasagiline-N-chloromethyl formate was added to a mixed solution of DIPEA, deoxycholic acid and TBAI in acetonitrile and DMF (20+5), followed by being stirred at 45° C. overnight. After the reaction liquid was rotated to dryness and added with EA for dissolution, a mixture was obtained. The mixture was successively washed with saturated NaCl (30 mL×2), 0.05 mol/L diluted HCl (30 mL×2), water (30 mL), saturated NaHCO$_3$ (30 mL) and saturated NaCl (30 mL), and dried by anhydrous sodium sulfate. After a filtration and rotation to dryness, 2.1 g of a white solid product was obtained through silica gel column chromatography (PE/EA=3:1 to 1:1), with a yield of 59.50%.

$^1$H-NMR(CDCl$_3$, 400 MHz) δ 7.25 (m, 2H), 7.18 (m, 2H), 5.85 (m, 2.55H), 5.65 (m, 0.45H), 4.12 (d, J=17.6 Hz, 0.45H), 3.98 (m, 1.55H), 3.60 (m, 1H), 3.57 (d, J=17.6 Hz, 0.45H), 3.48 (d, J=17.6 Hz, 0.55H), 3.06 (m, 1H), 2.87 (m, 1H), 2.45 (m, 2H), 2.35 (s, 1H), 2.27 (m, 2H), 2.17 (s, 0.45H), 2.11 (s, 0.55H), 1.82 (m, 5H), 1.61 (m, 10H), 1.40 (m, 7H), 1.26 (m, 2H), 1.11 (m, 3H), 0.98 (d, J=4.8 Hz, 3H), 0.91 (s, 3H), 0.67 (d, J=2.4 Hz, 3H).

ESI-MS, $C_{38}H_{53}NO_6$ (619.39), a measured value of 642.2 [M+Na]$^+$.

Example 12 Preparation of methyl ((Rasagiline-N-formyl)oxy)-icosanamidohexanoate

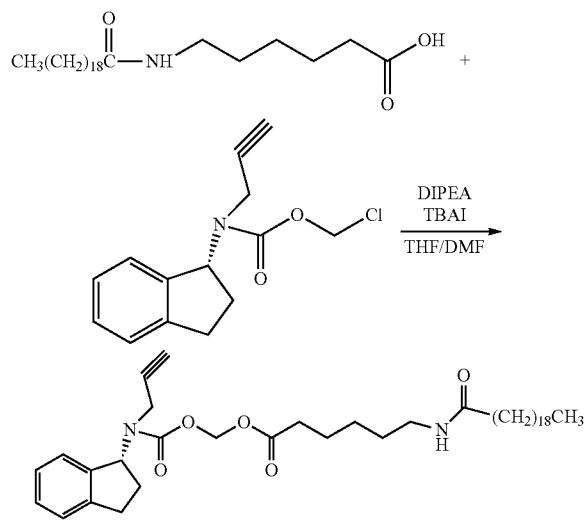

0.5 g of Rasagiline-N-chloromethyl formate was added to a mixed solution of 0.46 g of DIPEA, 0.5 g of icosanamidohexanoic acid and 100 mg of TBAI in THF/DMF (40+10 mL), followed by being stirred at 60° C. overnight. After the reaction liquid was rotated to dryness and added with isopropyl ether for dissolution, a mixture was obtained. The mixture was successively washed with 0.05 mol/L diluted HCl (30 mL×2), water (30 mL), saturated NaHCO$_3$ (30 mL) and saturated NaCl (30 mL), and dried by anhydrous sodium sulfate. After a filtration and rotation to dryness, 0.22 g of a white solid powder product was obtained through TLC (PE/EA=2:1), with a yield of 17.74%.

$^1$H-NMR(CDCl$_3$, 400 MHz) δ 7.25 (m, 2H), 7.18 (m, 2H), 5.85 (m, 2.5H), 5.66 (m, 0.5H), 5.54 (brs, 1H), 4.12 (d, J=23.6 Hz, 0.46H), 3.98 (d, J=23.6 Hz, 0.55H), 3.57 (d, J=23.6 Hz, 0.46H), 3.48 (d, J=23.6 Hz, 0.54H), 3.24 (m, 2H), 3.07 (m, 1H), 2.86 (m, 1H), 2.42 (m, 3H), 2.26 (m, 1H), 2.15 (t, J=10.4 Hz, 2H), 1.63 (m, 4H), 1.50 (m, 2H), 1.28 (m, 32H), 0.88 (t, J=8.8 Hz, 3H).

ESI-MS, C40H64N2O5 (652.48), a measured value of 653.5 [M+H]+.

Example 13 Preparation of methyl ((Rasagiline-N-formyl)oxy)-icosanamidobutanoate

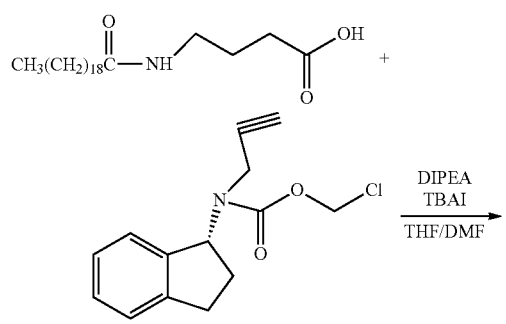

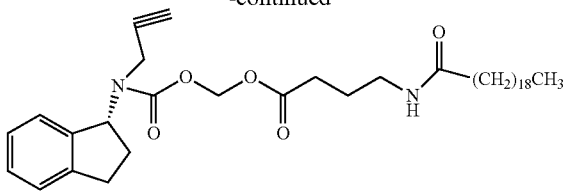

0.4 g of Rasagiline-N-chloromethyl formate was added to a mixed solution of 0.2 g of DIPEA, 0.2 g of 4-icosanamidobutanoic acid and 50 mg of TBAI in THF/DMF (40+10 mL), followed by being stirred at 60° C. overnight. After the reaction liquid was rotated to dryness and added with isopropyl ether for dissolution, a mixture was obtained. The mixture was successively washed with 0.05 mol/L diluted HCl (30 mL×2), water (30 mL), saturated NaHCO$_3$ (30 mL) and saturated NaCl (30 mL), and dried by anhydrous sodium sulfate. After a filtration and rotation to dryness, 0.15 g of a white solid powder product was obtained through TLC (PE/EA=2:1), with a yield of 15.95%.

$^1$H-NMR(CDCl$_3$, 400 MHz) δ 7.25 (m, 2H), 7.19 (m, 2H), 5.87 (m, 2H), 5.67 (m, 1H), 4.33 (brs, 1H), 4.11 (d, J=18.0 Hz, 0.44H), 3.98 (d, J=18.0 Hz, 0.56H), 3.58 (d, J=18.0 Hz, 0.44H), 3.48 (d, J=18.0 Hz, 0.56H), 3.29 (m, 2H), 3.07 (m, 1H), 2.86 (m, 1H), 2.44 (m, 3H), 2.24 (m, 1H), 2.15 (m, 3H), 1.86 (m, 2H), 1.57 (m, 2H), 1.25 (m, 32H), 0.88 (t, J=6.8 Hz, H).

ESI-MS, C$_{38}$H$_{60}$N$_2$O$_5$ (624.45), a measured value of 647.4 [M+Na]$^+$.

Example 14 Preparation of methyl ((Rasagiline-N-formyl)oxy)-stearamidobutanoate

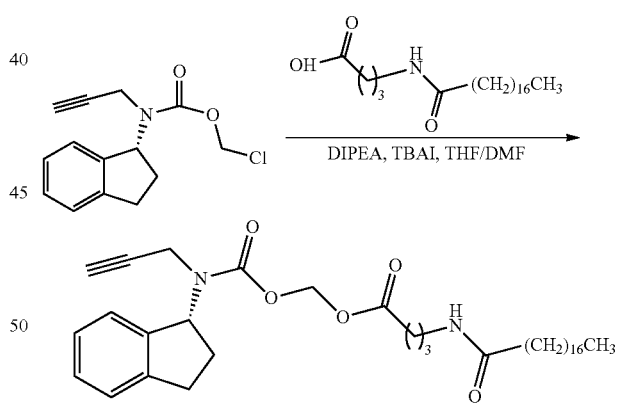

The methyl ((Rasagiline-N-formyl)oxy)-stearamidobutanoate was prepared according to the method of Example 13, the product was obtained as a white solid powder with a yield of 22.6%.

$^1$H NMR (CDCl$_3$, 400 MHz) δ 7.25 (m, 2H), 7.19 (m, 2H), 5.92-5.60 (m, 4H), 4.11 (d, J=18.0 Hz, 0.44H), 3.98 (d, J=18.0 Hz, 0.56H), 3.58 (d, J=18.0 Hz, 0.44H), 3.48 (d, J=18.0 Hz, 0.56H), 3.31 (m, 2H), 3.07 (m, 1H), 2.87 (m, 1H), 2.43 (m, 3H), 2.25 (m, 1H), 2.15 m, 3H), 1.87 (m, 2H), 1.60 (s, 2H), 1.25 (m, 28H), 0.88 (t, J=6.7 Hz, 3H).

ESI-MS, C$_{36}$H$_{56}$N$_2$O$_5$ (596.42), a measured value of 619.7 [M+Na]$^+$.

Example 15 Preparation of methyl ((Rasagiline-N-formyl)oxy)-palmitamidobutanoate

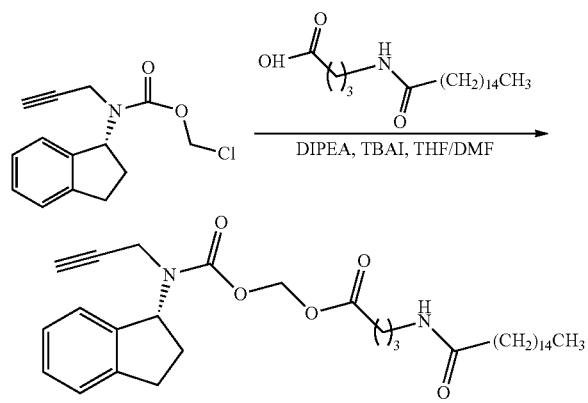

The methyl ((Rasagiline-N-formyl)oxy)-palmitamidobutanoate was prepared according to the method of Example 13, and the product was obtained as a white solid powder with a yield of 30.9%.

$^1$H NMR (CDCl$_3$, 400 MHz) δ 7.25 (m, 2H), 7.23-7.13 (m, 2H), 5.91-5.59 (m, 4H), 4.11 (d, J=18.0 Hz, 0.44H), 3.98 (d, J=18.0 Hz, 0.56H), 3.58 (d, J=18.0 Hz, 0.44H), 3.48 (d, J=18.0 Hz, 0.56H), 3.30 (m, 2H), 3.07 (m, 1H), 2.87 (m, 1H), 2.44 (m, 3H), 2.32-2.20 (m, 1H), 2.15 (m, 3H), 1.87 (m, 2H), 1.62 (m, 2H), 1.25 (s, 24H), 0.88 (t, J=6.7 Hz, 3H).

ESI-MS, C$_{34}$H$_{52}$N$_2$O$_5$ (568.39), a measured value of 591.4 [M+Na]$^+$.

Example 16 Preparation of methyl ((Rasagiline-N-formyl)oxy)4-dodecanamidobutanoate

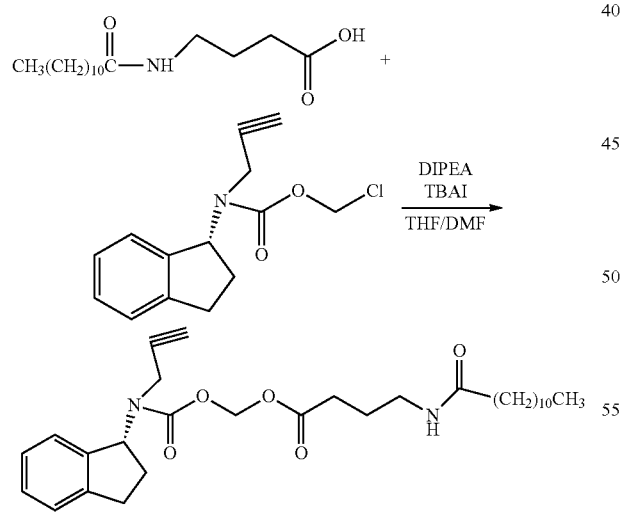

The methyl ((Rasagiline-N-formyl)oxy)4-dodecanamidobutanoate was prepared according to the method of Example 13, and the product was obtained as a white solid powder with a yield of 16.25%.

$^1$H NMR (CDCl$_3$, 400 MHz) δ 7.26-7.15 (m, 4H), 5.88-5.65 (m, 4H), 4.13 (d, J=18.0 Hz, 0.44H), 3.96 (d, J=18.0 Hz, 0.56H), 3.60 (d, J=18.0 Hz, 0.44H), 3.47 (d, J=18.0 Hz, 0.56H), 3.30 (t, 2H), 3.09 (m, 1H), 2.87 (m, 1H), 2.49-2.40 (m, 3H), 2.26-2.20 (m, 1H), 2.15 (t, 3H), 1.87 (m, 2H), 1.62-1.58 (m, 2H), 1.25 (s, 16H), 0.88 (t, J=6.7 Hz, 3H).

Example 17 Preparation of methyl ((Rasagiline-N-formyl)oxy)4-tetradecanamidobutanorate

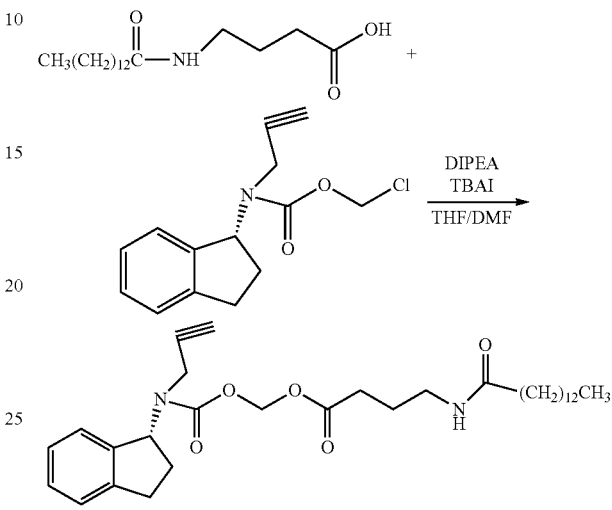

The methyl ((Rasagiline-N-formyl)oxy)4-tetradecanamidobutanoate was prepared according to the method of Example 13, and the product was obtained as a white solid powder with a yield of 23.80%.

1H NMR (CDCl3, 400 MHz) δ 7.26-7.15 (m, 4H), 5.87-5.65 (m, 4H), 4.13 (d, J=18.0 Hz, 0.44H), 3.96 (d, J=18.0 Hz, 0.56H), 3.60 (d, J=18.0 Hz, 0.44H), 3.47 (d, J=18.0 Hz, 0.56H), 3.30 (t, 2H), 3.07 (m, 1H), 2.87 (m, 1H), 2.44 (m, 3H), 2.26-2.22 (m, 1H), 2.15 (t, 3H), 1.87 (t, 2H), 1.60 (t, 2H), 1.25 (s, 20H), 0.88 (t, J=6.7 Hz, 3H).

Example 18 Preparation of methyl ((Rasagiline-N-formyl)oxy)4-stearamidohexanoate

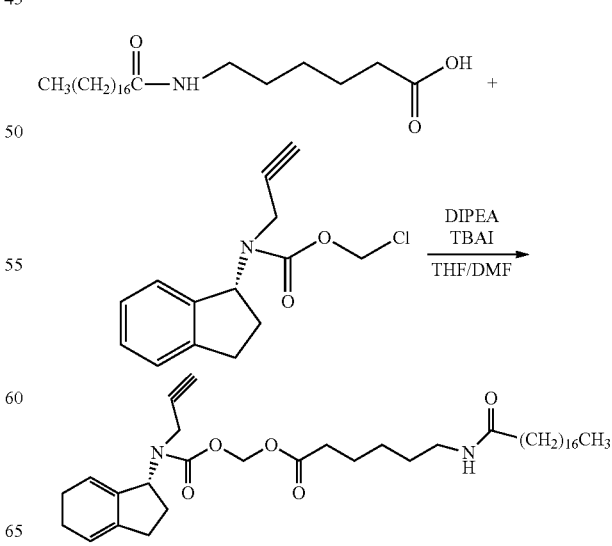

The methyl ((Rasagiline-N-formyl)oxy)4-stearamidohexanoate was prepared according to the method of Example 13, and the product was obtained ast a white solid powder with a yield of 15.90%.

1H NMR (CDCl3, 400 MHz) δ 7.26-7.17 (m, 4H), 5.87-5.48 (m, 4H), 4.14 (d, J=18.0 Hz, 0.44H), 3.96 (d, J=18.0 Hz, 0.56H), 3.60 (d, J=18.0 Hz, 0.44H), 3.46 (d, J=18.0 Hz, 0.56H), 3.20 (t, 2H), 3.06 (m, 1H), 2.86 (m, 1H), 2.46-2.35 (m, 3H), 2.29-2.20 (m, 1H), 2.16-2.12 (m, 3H), 1.68-1.52 (m, 4H), 1.38 (m, 2H), 1.26 (s, 30H), 0.88 (t, J=6.7 Hz, 3H).

Example 19 Preparation of methyl ((Rasagiline-N-formyl)oxy)4-stearoylglycinate

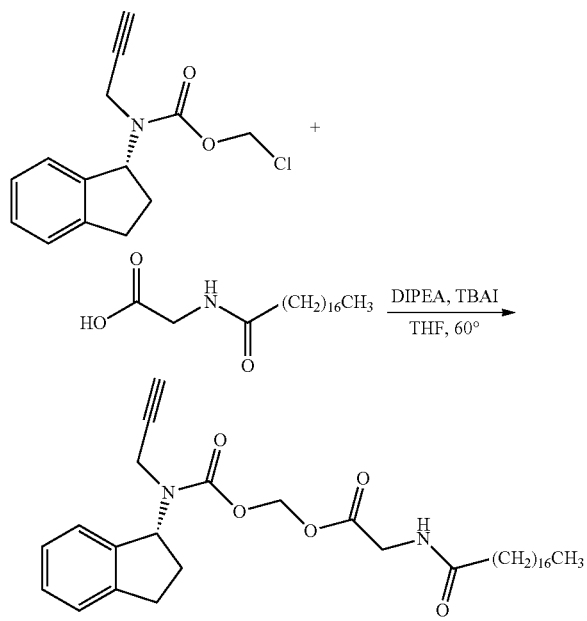

The methyl ((Rasagiline-N-formyl)oxy)4-stearoylglycinate was prepared according to the method of Example 13, and the product was obtained as a white solid powder with a yield of 51.38%.

1H NMR (CDCl3, 400 MHz) δ 7.26-7.16 (m, 4H), 5.94-5.80 (m, 4H), 4.14 (d, J=18.0 Hz, 0.44H), 3.93 (d, J=18.0 Hz, 0.56H), 3.62 (d, J=18.0 Hz, 0.44H), 3.46 (d, J=18.0 Hz, 0.56H), 3.30 (q, 2H), 3.07 (m, 1H), 2.87 (m, 1H), 2.53-2.41 (m, 1H), 2.26-2.21 (m, 3H), 2.17 (s, 1H), 1.65 (m, 2H), 1.25 (s, 24H), 0.88 (t, J=6.7 Hz, 3H).

Example 20 Preparation of methyl ((Rasagiline-N-formyl)oxy)4-docosanamidobutanoate

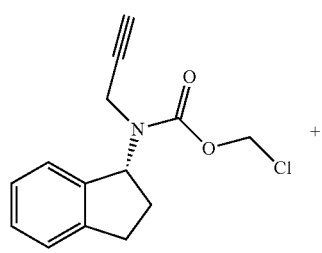

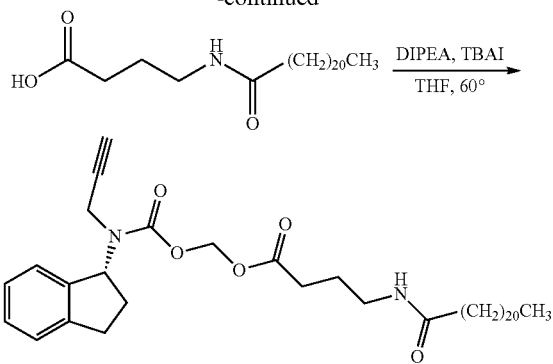

The methyl ((Rasagiline-N-formyl)oxy)4-docosanamidobutanoate was prepared according to the method of Example 13, and the product was obtained as a white solid powder with a yield of 31%.

1H NMR (CDCl3, 400 MHz) δ 7.21-7.26 (m, 2H), 7.17-7.20 (m, 2H), 5.81-5.88 (m, 2.56H), 5.65 (br, 1.44H), 4.11 (d, J=17.6 Hz, 0.44H), 3.98 (d, J=17.2 Hz, 0.56H), 3.58 (d, J=17.6 Hz, 0.44H), 3.49 (d, J=18.8 Hz, 0.56H), 3.30-3.31 (m, 2H), 3.03-3.11 (m, 1H), 2.83-2.89 (m, 1H), 2.43-2.49 (m, 3H), 2.22-2.27 (m, 1H), 2.13-2.17 (m, 3H), 1.84-1.89 (m, 2H), 1.57-1.63 (m, 2H), 1.25 (m, 36H), 0.88 (t, J=6.8 Hz, 3H).

Example 21 Preparation of methyl ((Rasagiline-N-formyl)oxy)5-palmitamidopentanoate

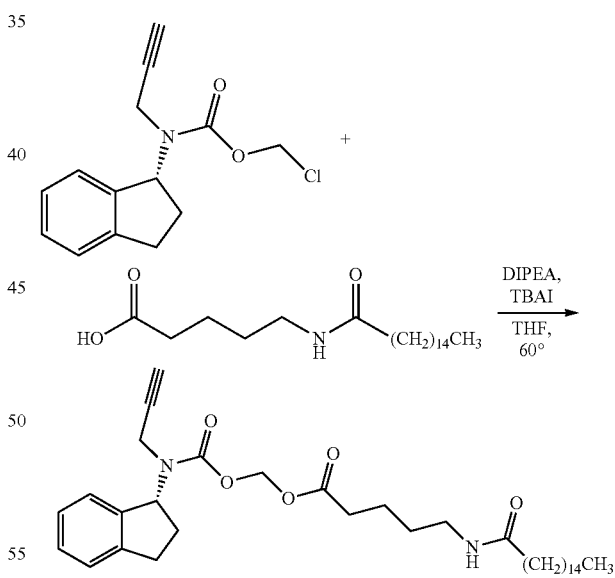

The methyl ((Rasagiline-N-formyl)oxy)5-palmitamidopentanoate was prepared according to the method of Example 13, and the product was obtained as a white solid powder with a yield of 17.6%.

1H NMR (CDCl3, 400 MHz) δ 7.21-7.26 (m, 2H), 7.15-7.19 (m, 2H), 5.81-5.87 (m, 2.55H), 5.65 (t, J=4.0 Hz, 0.45H), 5.54 (br, 1H), 4.11 (d, J=18.0 Hz, 0.45H), 3.98 (d, J=18.4 Hz, 0.55H), 3.57 (d, J=17.6 Hz, 0.45H), 3.48 (d, J=18.4 Hz, 0.55H), 3.25-3.27 (m, 2H), 3.03-3.10 (m, 1H), 2.81-2.91 (m, 1H), 2.38-2.45 (m, 3H), 2.21-2.29 (m, 1H), 2.13-2.17 (m, 3H), 1.65-1.71 (m, 2H), 1.56-1.62 (m, 4H), 1.25 (m, 26H), 0.89 (t, J=6.8 Hz, 3H).

Example 22 Preparation of methyl ((Rasagiline-N-formyl)oxy)5-stearamidopentanoate

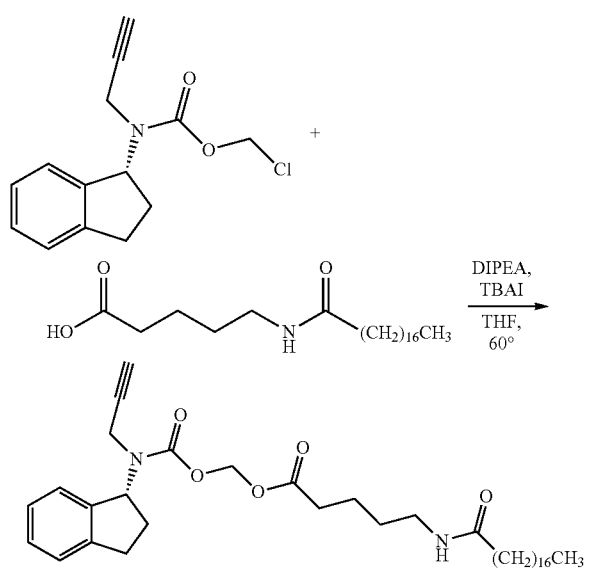

The methyl ((Rasagiline-N-formyl)oxy)5-stearamidopentanoate was prepared according to the method of Example 13, and the product was obtained as a white solid powder with a yield of 14.6%.

1H NMR (CDCl3, 400 MHz) δ 7.23-7.26 (m, 2H), 7.17-7.21 (m, 2H), 5.78-5.88 (m, 2.50H), 5.65 (t, J=4.0 Hz, 0.50H), 5.51 (br, 1H), 4.12 (d, J=18.4 Hz, 0.50H), 3.98 (d, J=18.4 Hz, 0.50H), 3.58 (d, J=17.2 Hz, 0.50H), 3.48 (d, J=15.6 Hz, 0.50H), 3.25-3.28 (m, 2H), 3.03-3.11 (m, 1H), 2.84-2.90 (m, 1H), 2.40-2.48 (m, 3H), 2.22-2.29 (m, 1H), 2.13-2.17 (m, 3H), 1.66-1.69 (m, 2H), 1.59-1.63 (m, 4H), 1.25 (m, 30H), 0.88 (t, J=6.8 Hz, 3H).

Example 23 Preparation of methyl ((Rasagiline-N-formyl)oxy)4-octadecylamidosuccinate

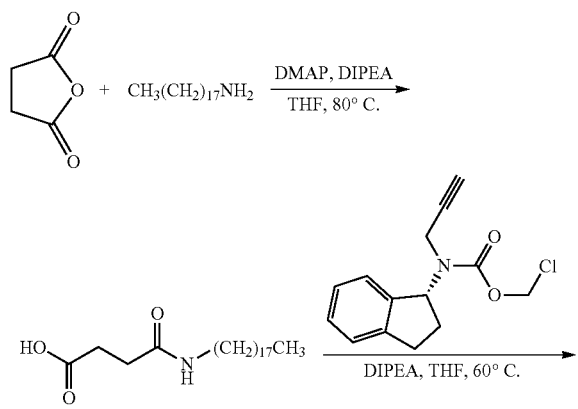

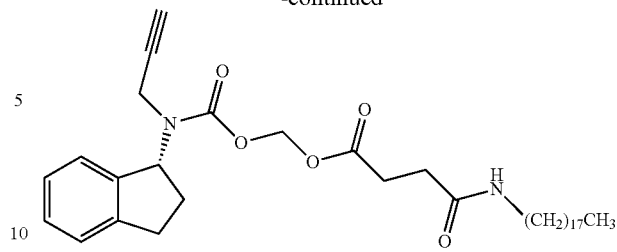

Octadecylamine (3.0 g, 11.13 mmol, 1.0 equivalent) and tetrahydrofuran (60 mL) were added to 250 mL of a single-neck flask, and then 4-dimethylaminopyridine (DMAP, 408 mg, 3.34 mmol, 0.3 equivalent), diisopropylethylamine (DIPEA, 2.87 g, 22.26 mmol, 2.0 equivalent) and succinic anhydride (1.36 g, 13.36 mmol, 1.2 equivalent) were further added to obtain a mixture. The mixture was kept stirring accompanied with heating reflux for 3 days. If it was detected by TLC that octadecylamine still exist and remain unchanged, the reaction was stopped and cooled to room temperature. A concentrated HCl was added for adjusting pH to 2-3, followed by suction filtration, a filtrate was collected. The filtrate was washed once by saturated salt solution. An organic phase was obtained, and it was dried by anhydrous sodium sulfate. After a filtration, rotation to dryness, drying through an oil pump, 2.7 g of a white solid crude product, that is 4-(octadecylamido) succinic acid, was obtained to be directly used in a next step.

4-(octadecylamido) succinic acid (2.7 g, 7.3 mmol, 1.0 equivalent) and 100 mL of tetrahydrofuran were added to 100 mL single-neck flask, and then diisopropylethylamine (DIPEA, 1.88 g, 14.6 mmol, 2.0 equivalent), Rasagiline-N-chloromethyl formate (2.31 g, 8.76 mmol, 1.2 equivalent) and tetrabutylammonium iodide (TBAI, 539 mg, 1.46 mmol, 0.2 equivalent) were added to obtain a mixture. The mixture was placed at 80° C. and kept stirring for 3.5 days. If it is detected by the TLC that there some raw materials still exist and remain unchanged, the reaction was stopped and cooled to room temperature. After a filtration, washing with ethyl acetate, and rotation to dryness, dichloromethane was used for dissolution, 1 M HCl aqueous solution was used to wash once, and anhydrous sodium sulfate was used for drying. After a filtration and rotation to dryness and separation through silica gel column chromatography (PE/EA=5:1 to PE/EA=1:1), fractions were combined and rotated to dryness, and then methanol was added for dissolution. Stirring was performed at −10° C. for crystallization until solids appear, followed by rapid suction filtration. An oil pump was used to dry the filter cake, and 200 mg of a while solid, that is methyl ((Rasagiline-N-formyl)oxy)4-octadecylamidosuccinate, was obtained with a yield of 4.6%.

$^1$H NMR (CDCl$_3$, 400 MHz) δ 7.23-7.26 (m, 2H), 7.18-7.22 (m, 2H), 5.79-5.89 (m, 2.56H), 5.59-5.67 (m, 1.44H), 4.11 (d, J=18.0 Hz, 0.44H), 3.97 (d, J=16.8 Hz, 0.56H), 3.58 (d, J=18.8 Hz, 0.44H), 3.47 (d, J=17.2 Hz, 0.56H), 3.20-3.25 (m, 2H), 3.03-3.10 (m, 1H), 2.83-2.91 (m, 1H), 2.72-2.78 (m, 2H), 2.45-2.48 (m, 3H), 2.24-2.26 (m, 1H), 2.16 (t, J=6.0 Hz, 1H), 1.48 (m, 2H), 1.25 (m, 28H), 0.88 (t, J=6.8 Hz, 3H).

Example 24 Detection of Physicochemical Properties of the Prodrug of Rasagiline

A melting point and solubility (phosphate buffer with pH of 7.4) of synthesized prodrug compounds of Rasagiline were detected, and the results are shown in table 1:

It can be noted based on data from the below table that the compound of the present disclosure has a higher melting point with respect to the control group, in particular to Examples 8, 12, 13, 14, 15, 17, 20 and 23.

TABLE 1

DATA OF MELTING POINT AND SOLUBILITY OF A PRODRUG COMPOUND OF RASAGILINE

| NUMBER | EXMAPLE | MELTING POINT(° C.) | SOLUBILITY (μg/ml) |
|---|---|---|---|
| 1 | 1 (CONTROL) | <25 | <5 |
| 2 | 2 | 66-70 | <5 |
| 3 | 3 (CONTROL) | <25 | <5 |
| 4 | 4 | <25 | <5 |
| 5 | 5 (CONTROL) | <25 | <5 |
| 6 | 6 | <50 | <5 |
| 7 | 7 | / | 31.7 |
| 8 | 8 | 130.4-133.8 | <5 |
| 9 | 9 | <50 | <5 |
| 10 | 10 | <50 | <5 |
| 11 | 11 | <50 | <5 |
| 12 | 12 | 77.2-80.8 | <5 |
| 13 | 13 | 80-82 | <5 |
| 14 | 14 | 76-78 | <5 |
| 15 | 15 | 73-75 | <5 |
| 16 | 16 | 56.1-59.4 | <5 |
| 17 | 17 | 66.3-71.8 | <5 |
| 18 | 18 | 58.9-64.2 | <5 |
| 19 | 20 | 87.4-87.8 | <5 |
| 20 | 21 | 55.4-56.2 | <5 |
| 21 | 22 | 58.3-58.9 | <5 |
| 22 | 23 | 75.3-77.1 | <5 |

Example 25 Pharmacokinetics Experiment of Prodrug of Rasagiline in the Body

One common male beagle was used for each group, and they were forbidden to eat for 12 hours before administering drugs, and drank water freely meanwhile. Injectable suspensions of Example 13, Example 15, Example 14, Example 20, Example 8 were intramuscularly injected in a dosage of 0.47 mg/kg Rasagiline (1.72 mg/kg, 1.56 mg/kg, 1.64 mg/kg, 1.80 mg/kg, 1.16 mg/kg of prodrug respectively after conversion). Before administering drugs and 1 hour, 2 hours, 4 hours, 8 hours, 12 hours, 18 hours, 24 hours, 48 hours, 96 hours, 144 hours, 192 hours, 240 hours, 288 hours, and 360 hours after drug administration, 1.0 mL whole blood of the beagle was collected from venous vein in front legs each time and centrifuged in an heparinized centrifuge tube at 6000 rpm for 10 minutes at 4° C., to separate blood plasma, and the blood plasma was stored to be measured at −80° C. Treatment of blood plasma sample: The blood plasma sample was placed in an ice bath; 30 μL of methanol and 20 μL of interior label (2 μg/mL apigenin dissolved in 50% methanol) were added into 200 μL of the blood plasma sample and mixed through vortex, and then 4 mL of ethyl acetate was added and mixed through vortex. After being centrifuged at 9000 g for 2 minutes, an organic phase was separated and dried in vacuum, and then 150 μL of methanol was added for re-dissolution. 30 μL of a prepared sample was taken for analyzing.

Data analysis: The sample was detected by LC-MS/MS, and analyzed by a DAS 2.0 software to calculate pharmacokinetic parameters according to blood drug concentration, providing parameters such as AUC (0-t), AUC(0-∞), MRT (0-t), MRT(0-∞), $C_{max}$, $T_{max}$, and $t_{1/2}$, etc.

Experimental results: after the beagles was respectively administered the above described prodrugs of Rasagiline, the blood drug concentration of the Rasagiline is shown in Table 2. FIG. 1 is made according to data from the Table 2. It can be noted from the table 2 and table 3 that the compound of the present disclosure may be slowly, sustainably and steady released and converted into Rasagiline, achieving an effect of long-acting treatment. In particular, the releases of the prodrugs of Example 13 and Example 20 are steadier, which can well meet the requirement of the long-acting injectable suspensions. Although the prodrugs of Example 14 and Example 15 are released rapidly within 2 days after the prodrugs were administered, they are released steady after that, thus both of these two examples achieve a long-acting effect.

TABLE 2

BLOOD DRUG CONCENTRATIONS OF RASAGILINE AFTER PRODRUGS OF RASAGILINE ARE INTRAMUSCULARLY INJECTED INTO BEAGLE DOGS

| | Blood drug concentration of Rasagiline (ng/mL) | | | | |
|---|---|---|---|---|---|
| t(h) | EXAMPLE 15 | EXAMPLE 14 | EXAMPLE 8 | EXAMPLE 13 | EXAMPLE 20 |
| 0.5 | 1.03 | 0.937 | 2.11 | 0.037 | 0.032 |
| 1 | 1.17 | 3.79 | 6.62 | 0.057 | 0.036 |
| 2 | 1.12 | 2.4 | 8.82 | 0.061 | 0.037 |
| 4 | 0.928 | 2.11 | 9.39 | 0.081 | 0.025 |
| 8 | 2.39 | 3.33 | 4.19 | 0.128 | 0.066 |
| 12 | 1.16 | 0.463 | 2.21 | 0.195 | 0.101 |
| 18 | 2.23 | 1.58 | 3.05 | 0.192 | 0.101 |
| 24 | 2.32 | 3.02 | 3.23 | 0.21 | 0.148 |
| 48 | 0.892 | 0.739 | 2.43 | 0.425 | 0.198 |
| 96 | 0.852 | 0.476 | 0.532 | 0.44 | 0.333 |
| 144 | 0.616 | 0.0803 | 0.385 | 0.224 | 0.325 |
| 192 | 0.199 | 0 | 0.238 | 0.172 | 0.214 |
| 240 | 0 | 0 | 0.167 | 0.138 | 0.23 |
| 288 | 0.0277 | 0 | 0.149 | 0.145 | 0.165 |
| 360 | 0 | 0 | 0 | 0.095 | 0.126 |

After beagles were intramuscularly injected with the above described prodrugs of Rasagiline, pharmacokinetic parameters of the Rasagiline are shown in TABLE 3.

TABLE 3

PHARMACOKINETIC PARAMETERS OF THE RASAGILINE AFTER THE PRODRUGS OF RASAGILINE ARE INTRAMUSCULARLY INJECTED INTO BEAGLES

| PARAMETERS | UNITS | EXAMPLE 15 | EXAMPLE 14 | EXAMPLE 8 | EXAMPLE 13 | EXAMPLE 20 |
|---|---|---|---|---|---|---|
| $AUC_{(0-t)}$ | μg/L*h | 187.6 | 135 | 296.5 | 87.7 | 92.8 |
| $AUC_{(0-\infty)}$ | μg/L*h | 188.9 | 138.4 | 319 | 94.5 | 124.3 |
| $MRT_{(0-t)}$ | h | 75.1 | 38.3 | 55.2 | 162.5 | 208.4 |
| $MRT_{(0-\infty)}$ | h | 76.9 | 41.9 | 82.2 | 204.4 | 364 |
| $t_{1/2z}$ | h | 32.4 | 29.5 | 104.8 | 122.3 | 237.2 |
| $T_{max}$ | h | 8 | 1 | 4 | 64 | 96 |
| $C_{max}$ | μg/L | 2.39 | 3.79 | 9.39 | 0.497 | 0.333 |

Although the present invention has been disclosed in the form of preferred embodiments and variations thereon, it will be understood that numerous additional modifications and variations could be made thereto without departing from the scope of the invention.

The invention claimed is:
1. A long-acting prodrug of Rasagiline or a stereoisomer, or solvate thereof, wherein the long-acting prodrug of Rasagiline has a structure of formula I:

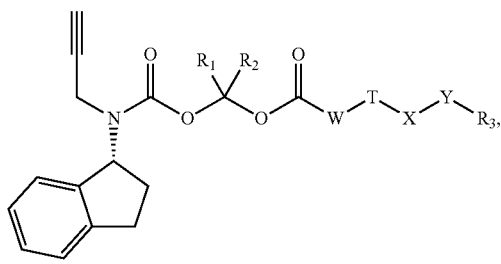

wherein,
both T and W are absent;
each of $R_1$ and $R_2$ is independently selected from H, D, or $C_{1-4}$ alkyl;
X is selected from $(CH_2)_m$, wherein m is an integer selected from 1 to 10;
Y is selected from —C(=O)NH—, or —NHC(=O)—; and
$R_3$ is selected from linear or branched, saturated or unsaturated $C_7$-$C_{27}$ alkyl.

2. The long-acting prodrug of Rasagiline or a stereoisomer, or solvate thereof according to claim 1, wherein $R_1$ is H or D, $R_2$ is methyl, H or D; each of $R_1$ and $R_2$ is independently H, D, or methyl.

3. The long-acting prodrug of Rasagiline or a stereoisomer, or solvate thereof according to claim 1, wherein $R_3$ is —CH=CHR$_4$, wherein $R_4$ is selected from phenyl substituted with one or more groups selected from OH, or alkoxy.

4. The long-acting prodrug of Rasagiline or a stereoisomer, or solvate thereof according to claim 1, wherein the long-acting prodrug of Rasagiline is selected from one of the following compounds:

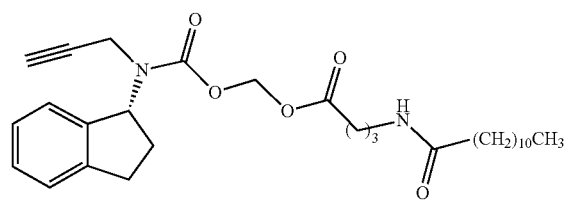

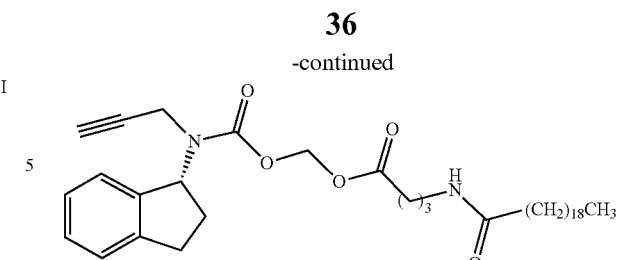

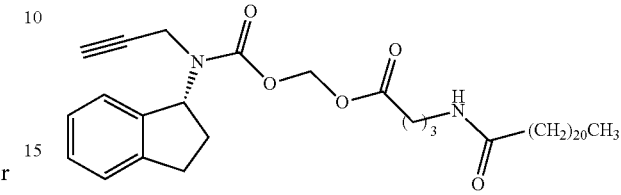

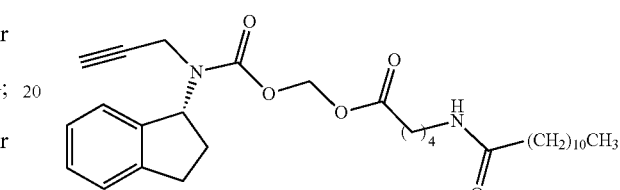

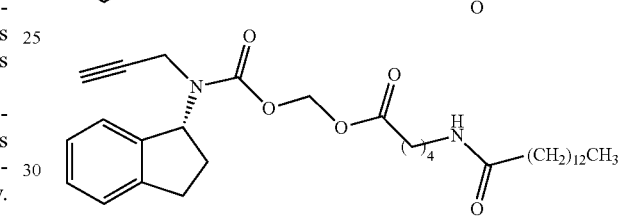

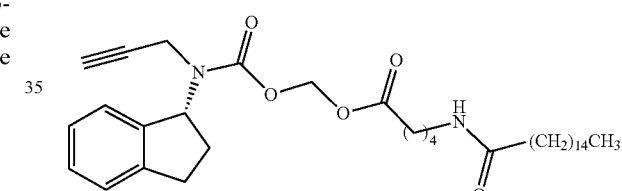

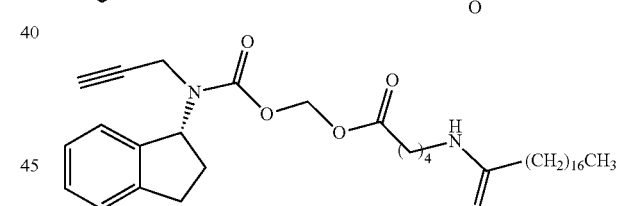

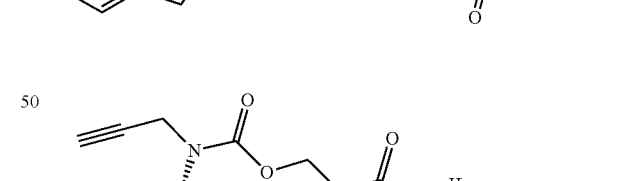

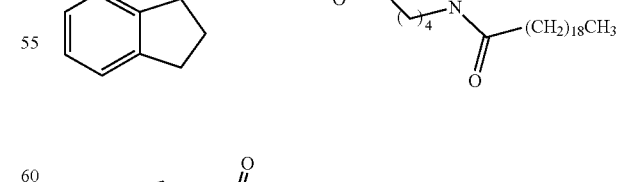

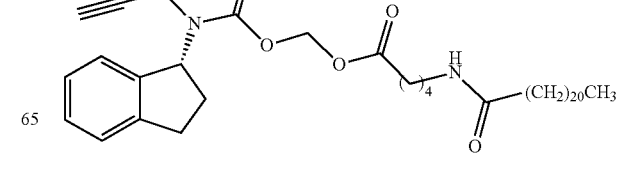

-continued

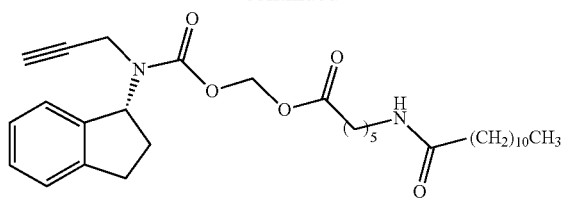

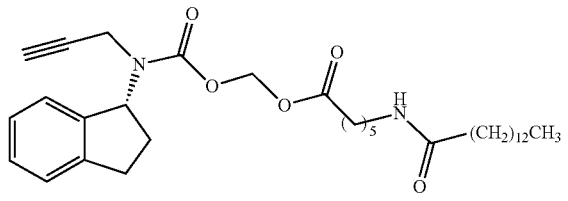

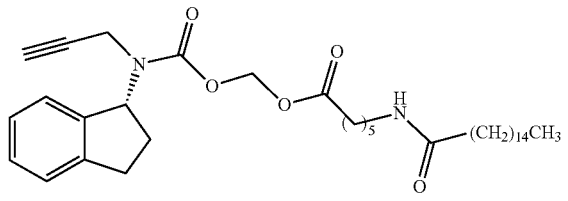

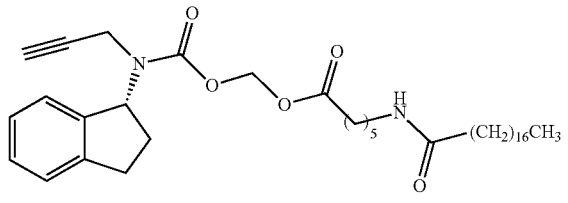

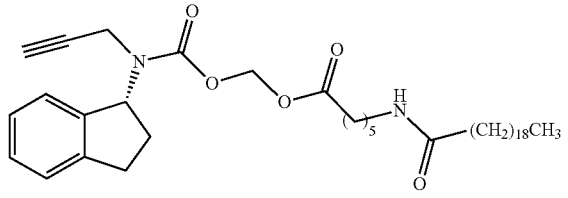

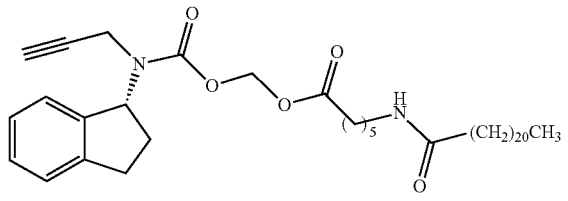

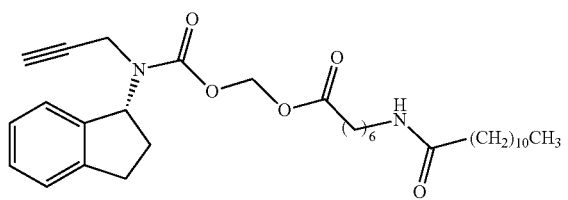

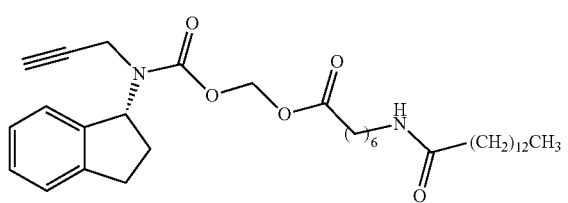

-continued

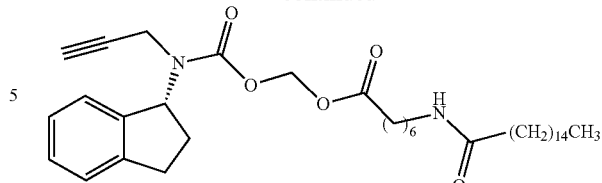

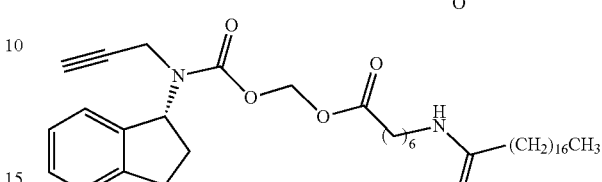

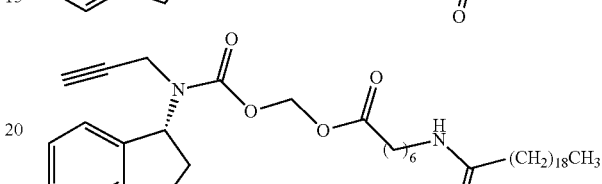

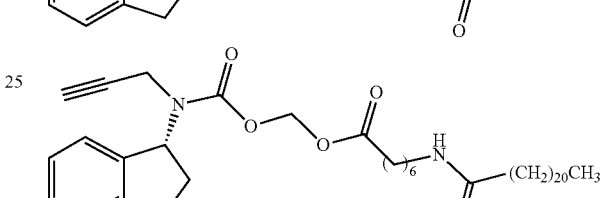

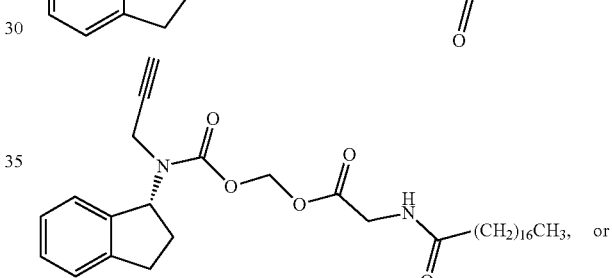

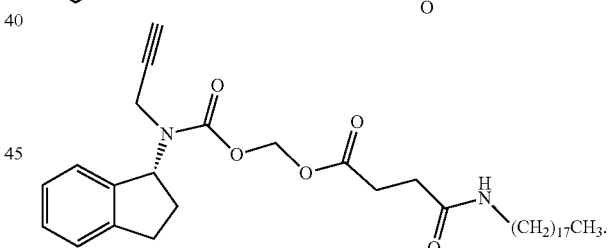

5. A pharmaceutical composition, comprising the prodrug of Rasagiline or a stereoisomer, or solvate thereof according to claim 1, and a pharmaceutically acceptable carrier or excipient.

6. A method of preventing and/or treating a central nervous system disease in a subject in need thereof, comprising administering the prodrug of Rasagiline or a stereoisomer, or solvate thereof according to claim 1, or the pharmaceutical composition wherein, the medicament is a long-acting drug.

7. The method according to claim 6, wherein the central nervous system disease is Parkinson's disease.

8. A long-acting prodrug of Rasagiline or a stereoisomer, or solvate thereof, wherein the prodrug of Rasagiline has a structure of formula II:

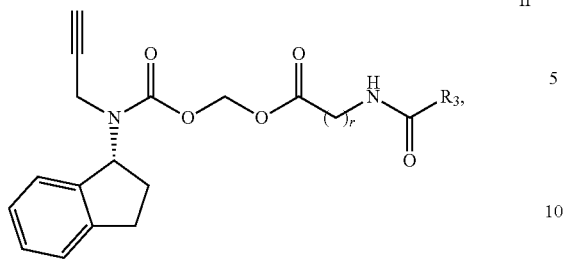
II
wherein r is an integer from 1 to 10 and $R_3$ is linear $C_7$-$C_{27}$ alkyl;
wherein r is an integer from 1 to 6 and $R_3$ is linear $C_9$-$C_{25}$ alkyl; or
wherein r is an integer from 3 to 6 and $R_3$ is linear $C_{11}$-$C_{25}$ alkyl or $R_3$ is linear $C_{11}$-$C_{21}$ alkyl.
* * * * *